United States Patent
Yoshikuni et al.

(10) Patent No.: US 9,260,403 B2
(45) Date of Patent: Feb. 16, 2016

(54) METHODS FOR PREPARING 2,5-FURANDICARBOXYLIC ACID

(71) Applicants: Yasuo Yoshikuni, Albany, CA (US);
Susan R. Cooper, Berkeley, CA (US);
Adam J. Wargacki, Berkeley, CA (US);
Leo E. Manzer, Wilmington, DE (US);
James F. White, Richland, WA (US);
Lou Kapicak, South Charleston, WV (US); Dennis J. Miller, Okemos, MI (US); Lars Peereboom, Haslett, MI (US)

(72) Inventors: Yasuo Yoshikuni, Albany, CA (US);
Susan R. Cooper, Berkeley, CA (US);
Adam J. Wargacki, Berkeley, CA (US);
Leo E. Manzer, Wilmington, DE (US);
James F. White, Richland, WA (US);
Lou Kapicak, South Charleston, WV (US); Dennis J. Miller, Okemos, MI (US); Lars Peereboom, Haslett, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 0 days.

(21) Appl. No.: 14/229,388

(22) Filed: Mar. 28, 2014

(65) Prior Publication Data
US 2014/0295508 A1 Oct. 2, 2014

Related U.S. Application Data

(63) Continuation of application No. PCT/US2012/058109, filed on Sep. 28, 2012.

(60) Provisional application No. 61/541,035, filed on Sep. 29, 2011, provisional application No. 61/541,038, filed on Sep. 29, 2011.

(51) Int. Cl.
*C07D 307/68* (2006.01)

(52) U.S. Cl.
CPC .................. *C07D 307/68* (2013.01)

(58) Field of Classification Search
CPC .................................................. C07D 307/68
See application file for complete search history.

(56) References Cited

FOREIGN PATENT DOCUMENTS

| EP | 2 033 958 A1 | 3/2009 |
|---|---|---|
| WO | WO-2009/008756 A2 | 1/2009 |
| WO | WO-2010/144873 A1 | 12/2010 |
| WO | WO-2011/081658 A2 | 7/2011 |
| WO | WO-2011/088422 A2 | 7/2011 |

OTHER PUBLICATIONS

Feather and Harris (J. Org. Chem., 31 (12):4018-4021 (1996)).*
Tong et al. (Appl. Catal. A-Gen, 385:1-13 (2010).*
International Search Report for corresponding International Application No. PCT/US2012/058109, dated Jan. 24, 2013 (2 pages).
Preiss J., and Ashwell G., "Alginic Acid Metabolism in Bacteria," *J. Biol. Chem.*, 237(2):309-16 (1962).
Feather M.S., and Harris J.F., "Relationships Between Some Uronic Acids and Their Decarboxylation Products," *J. Org. Chem.*, 31(12):4018-21 (1966).
Condemine G., Hugouvieux-Cotte-Pattat N., and Robert-Baudouy J., "Isolation of Erwinia chrysanthemi kduD Mutants Altered in Pectin Degradation," *J. Bacteriol.*, 165(3):937-41 (1986).
Tong X., Ma Y. and Li Y., "Biomass Into Chemicals: Conversion of Sugars to Furan Derivatives by Catalytic Processes," *Appl. Catal. A-Gen*, 385:1-13 (2010).

* cited by examiner

*Primary Examiner* — Valerie Rodriguez-Garcia
(74) *Attorney, Agent, or Firm* — Marshall, Gerstein & Borun LLP

(57) ABSTRACT

Provided are methods of producing 2,5-furandicarboxylic acid (FDCA) from renewable sources such as seaweed, alginate, oligoalginate, pectin, oligopectin, polygalacturonate, galacturonate, and/or oligogalacturonate. The sugars in the renewable sources can be converted into one or more intermediates such as 4-deoxy-L-erythro-5-hexoseulose uronate (DEHU), 4-deoxy-L-threo-5-hexosulose uronate (DTHU), 5-hydroxymethyl furfural (HMF), 2,5-dihydroxymethyl furan (DHMF), and 5-formyl-2-furancarboxylic acid (FFA), which can be converted into FDCA by dehydration and cyclization to produce 5-formyl-2-furancarboxylic acid (FFA), followed by oxidation to produce FDCA. DEHU or DTHU may also be converted into FDCA by oxidation to produce 2,3-dihydroxy-5-oxohexanedioic acid (DOHA), which then undergoes dehydration and cyclization to produce FDCA.

36 Claims, 22 Drawing Sheets

METHODS FOR PREPARING 2,5-FURANDICARBOXYLIC ACID

CROSS-REFERENCE TO RELATED APPLICATIONS

This application is a continuation of International Patent Application No. PCT/US2012/058109 designating the United States and filed Sep. 28, 2012, which claims the priority benefit of U.S. Provisional Patent Application Nos. 61/541,035 and 61/541,038, both of which were filed Sep. 29, 2011, all of which are incorporated herein by reference in their entireties.

FIELD

The present disclosure relates generally to methods for preparing 2,5-furandicarboxylic acid (FDCA), and more specifically to methods for preparing FDCA from sources such as seaweed, alginate, oligoalginate, alginate monomers (e.g., mannuronate, guluronate, and 4-deoxy-L-erythro-5-hexoseulose uronate), pectin, polygalacturonate, oligogalacturonate, and pectin monomers (e.g., galacturonate and 4-deoxy-L-threo-5-hexosulose urinate).

BACKGROUND

There exists a high demand to produce 2,5-furandicarboxylic acid (FDCA) from renewable sources. FDCA is an attractive alternative to terephthalic acid in producing polyethylene terephthalate (PET), which is used to manufacture polyester fabrics. Additionally, FDCA may also serve as a precursor for adipic acid, which in turn may be used to produce nylons. FDCA may also serve as a precursor for jet fuels (e.g., Jet-A), as well as other diol-, diamine-, or dialdehyde-based chemicals.

Currently, several methods are known for synthesizing FDCA. For example, FDCA may be produced by dehydration of hexose derivatives. Hexose such as fructose or glucose can undergo acid-catalyzed dehydration to form 5-hydroxymethylfurfural (HMF), which is then oxidized to produce FDCA. These reactions, however, are generally not selective and yield a number of side products, such as humin, levulinic acid and formic acid. Furthermore, HMF may undergo polymerization under the oxidation reaction conditions to produce FDCA. Due to these various side product reactions, the yields for FDCA from hexose derivatives are typically quite low.

FDCA may also be produced by oxidation of 2,5-disubstituted furans, and by catalytic conversion of various furan derivatives. Yields for these reactions are also typically low, or may require harsh reaction conditions that are not suitable for commercial production.

Thus, what is needed in the art is a commercially-viable method of producing FDCA from renewable resources, such as seaweed, alginate or pectin.

BRIEF SUMMARY

The present disclosure addresses this need by providing methods to produce 2,5-furandicarboxylic acid (FDCA) from 4-deoxy-L-erythro-5-hexoseulose uronate (DEHU) or 4-deoxy-L-threo-5-hexosulose uronate (DTHU), which may be obtained from alginate or pectin.

In one aspect, the present disclosure provides a method A of producing 2,5-furandicarboxylic acid (FDCA) by: a) providing 4-deoxy-L-erythro-5-hexoseulose uronate (DEHU); b) converting the DEHU into 5-formyl-2-furancarboxylic acid (FFA); and c) oxidizing the FFA to produce FDCA. In some embodiments of method A, the method further includes isolating the FDCA. In some embodiments that may be combined with any of the preceding embodiments of method A, the FDCA is used as a precursor for producing adipic acid.

In some embodiments that may be combined with any of the preceding embodiments of method A, the converting of the DEHU into FFA involves dehydrating and cyclizing the DEHU. In certain embodiments of method A, DEHU is converted into FFA by combining the DEHU with a catalyst to form a reaction mixture. In some embodiments that may be combined with any of the preceding embodiments of method A, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method A, the catalyst is an inorganic acid, such as phosphoric acid, sulfuric acid, or hydrochloric acid. In one embodiment of method A, the catalyst is sulfuric acid. In yet another embodiment of method A, the catalyst is an ion-exchange resin.

In some embodiments that may be combined with any of the preceding embodiments of method A, the converting of the DEHU into FFA is performed neat. In other embodiments of method A, the reaction mixture that includes the DEHU and the catalyst is combined with a solvent. In some embodiments of method A, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In certain embodiments of method A, the solvent is water or methanol. In one embodiment of method A, the solvent is water.

In some embodiments that may be combined with any of the preceding embodiments of method A, the converting of the DEHU into FFA may further include heating the reaction mixture. In certain embodiments of method A, the reaction mixture is heated to a temperature between 50° C. and 500° C.

In some embodiments that may be combined with any of the preceding embodiments of method A, the oxidizing of FFA to produce FDCA involves combining the FFA with an oxidant. The oxidation reaction may be catalyzed or uncatalyzed. In certain embodiments of method A, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method A, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method A, the oxidation catalyst is platinum on carbon. In some embodiments that may be combined with any of the preceding embodiments of method A, the oxidizing of FFA to produce FDCA further involves combining the FFA and the oxidant within water.

In some embodiments that may be combined with any of the preceding embodiments of method A, the DEHU is obtained from alginate. In other embodiments that may be combined with any of the preceding embodiments of method A, the method yields at least 20% of the theoretical maximum of FDCA that may be produced from DEHU.

In another aspect, the present disclosure provides a method B of producing 2,5-furandicarboxylic acid (FDCA) by: a) providing 4-deoxy-L-erythro-5-hexoseulose uronate (DEHU); b) oxidizing the DEHU to produce 2,3-dihydroxy-5-oxohexanedioic acid (DOHA); and c) converting the DOHA into FDCA. In embodiment of method B, the DOHA is (2S)-DOHA. In some embodiments that may be combined with any of the preceding embodiments of method B, the method further includes isolating the FDCA. In some embodiments of method B, the FDCA is used as a precursor for producing adipic acid.

In some embodiments that may be combined with any of the preceding embodiments of method B, the oxidizing of DEHU to produce DOHA involves combining the DEHU with an oxidant. The oxidation reaction may be catalyzed or uncatalyzed. In certain embodiments of method B, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method B, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method B, the oxidation catalyst is platinum on carbon. In some embodiments that may be combined with any of the preceding embodiments of method B, the oxidizing of DEHU to produce DOHA further involves combining the DEHU and the oxidant in water.

In some embodiments that may be combined with any of the preceding embodiments of method B, the converting of the DOHA into FDCA involves dehydrating and cyclizing the DOHA. In certain embodiments of method B, DOHA is converted into FDCA by combining DOHA with a catalyst to form a reaction mixture. In some embodiments that may be combined with any of the preceding embodiments of method B, the catalyst is an acid. Suitable catalysts may include, for example, oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method B, the catalyst is an inorganic acid, such as phosphoric acid, sulfuric acid, or hydrochloric acid. In one embodiment of method B, the catalyst is sulfuric acid. In yet another embodiment of method B, the catalyst is an ion-exchange resin.

In some embodiments that may be combined with any of the preceding embodiments of method B, the converting of the DOHA into FDCA is performed neat. In other embodiments of method B, the reaction mixture is combined with a solvent. In certain embodiments of method B, the solvent is C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In some embodiments of method B, the solvent is water or methanol.

In some embodiments that may be combined with any of the preceding embodiments of method B, the converting of the DOHA into FDCA may further include heating the reaction mixture. In certain embodiments of method B, the reaction mixture is heated to a temperature between 50° C. and 500° C.

In some embodiments that may be combined with any of the preceding embodiments of method B, the DEHU is obtained from alginate. In other embodiments that may be combined with any of the preceding embodiments of method B, the method yields at least 20% of the theoretical maximum of FDCA that may be produced from DEHU.

In another aspect, the present disclosure provides a method C of producing 2,5-furandicarboxylic acid (FDCA) by: a) providing 4-deoxy-L-threo-5-hexosulose uronate (DTHU); b) converting DTHU into 5-formyl-2-furancarboxylic acid (FFA); and c) oxidizing the FFA to produce FDCA. In some embodiments of method C, the method further includes isolating the FDCA. In some embodiments that may be combined with any of the preceding embodiments of method C, the FDCA is used as a precursor for producing adipic acid.

In some embodiments of method C, the converting of DTHU into FFA involves dehydrating and cyclizing the DTHU. In certain embodiments of method C, DTHU is converted into FFA by combining the DTHU with a catalyst to form a reaction mixture. In some embodiments that may be combined with any of the preceding embodiments of method C, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method C, the catalyst is an inorganic acid, such as phosphoric acid, sulfuric acid, or hydrochloric acid. In one embodiment of method C, the catalyst is sulfuric acid. In yet another embodiment of method C, the catalyst is an ion-exchange resin.

In some embodiments that may be combined with any of the preceding embodiments of method C, the converting of DTHU into FFA is performed neat. In other embodiments of method C, the reaction mixture is combined with a solvent. In some embodiments of method C, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof.

In some embodiments that may be combined with any of the preceding embodiments of method C, the converting of DTHU into FFA may further include heating the reaction mixture. In certain embodiments of method C, the reaction mixture is heated to a temperature between 50° C. and 500° C.

In some embodiments that may be combined with any of the preceding embodiments of method C, the oxidizing of FFA to produce FDCA involves combining the FFA with an oxidant. The oxidation reaction may be catalyzed or uncatalyzed. In certain embodiments of method C, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method C, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method C, the oxidation catalyst is platinum on carbon. In some embodiments that may be combined with any of the preceding embodiments of method C, the oxidizing of FFA to produce FDCA further involves combining the FFA and the oxidant within water.

In some embodiments that may be combined with any of the preceding embodiments of method C, the DTHU is obtained from pectin. In other embodiments that may be combined with any of the preceding embodiments of method C, the method yields at least 20% of the theoretical maximum of FDCA that may be produced from DTHU.

In another aspect, the present disclosure provides a method D of producing 2,5-furandicarboxylic acid (FDCA) by: a) providing 4-deoxy-L-threo-5-hexosulose uronate (DTHU); b) oxidizing DTHU to produce 2,3-dihydroxy-5-oxohexanedioic acid (DOHA); and c) converting the DOHA into FDCA. In embodiment of method D, the DOHA is (2R)-DOHA. In some embodiments of method D, the method further includes isolating the FDCA. In some embodiments that may be combined with any of the preceding embodiments, the FDCA is used as a precursor for producing adipic acid.

In some embodiments that may be combined with any of the preceding embodiments of method D, the oxidizing of DTHU to produce DOHA involves combining the DTHU with an oxidant. The oxidation reaction may be catalyzed or uncatalyzed. In certain embodiments of method D, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method D, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method D, the oxidation catalyst is platinum on carbon. In some embodiments that may be combined with any of the preceding embodiments of method D, the oxidizing of DTHU to produce DOHA further involves combining the DTHU and the oxidant in water.

In some embodiments that may be combined with any of the preceding embodiments of method D, the converting of the DOHA into FDCA involves dehydrating and cyclizing the DOHA. In certain embodiments of method D, DOHA is converted into FDCA by combining DOHA with a catalyst to form a reaction mixture. In some embodiments that may be combined with any of the preceding embodiments of method D, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method D, the catalyst is an inorganic acid, such as phosphoric acid, sulfuric acid, or hydrochloric acid. In one embodiment of method D, the catalyst is sulfuric acid. In yet another embodiment of method D, the catalyst is an ion-exchange resin.

In some embodiments that may be combined with any of the preceding embodiments of method D, the converting of the DOHA into FDCA is performed neat. In some embodiments of method D, the reaction mixture is combined with a solvent. In certain embodiments of method D, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In some embodiments of method D, the solvent is water or methanol.

In some embodiments that may be combined with any of the preceding embodiments of method D, the converting of the DOHA into FDCA may further include heating the reaction mixture. In certain embodiments of method D, the reaction mixture is heated to a temperature between 50° C. and 500° C.

In some embodiments that may be combined with any of the preceding embodiments of method D, the DTHU is obtained from pectin. In other embodiments that may be combined with any of the preceding embodiments of method D, the method yields at least 20% of the theoretical maximum of FDCA that may be produced from DTHU.

In some of the foregoing embodiments, the methods are carried out in a single reaction vessel. In other embodiments, the reaction intermediates are used in the next step of the process without isolation or purification. In yet other embodiments, the reaction steps are carried out using a continuous flow reactor. In alternative embodiments, certain reaction intermediates (e.g. FFA, DOHA) are isolated prior to the next reaction.

In another aspect, the present disclosure provides a method E of producing 5-formyl-2-furancarboxylic acid (FFA), by: a) providing 4-deoxy-L-erythro-5-hexoseulose uronate (DEHU) or 4-deoxy-L-threo-5-hexosulose uronate (DTHU); and b) converting the DEHU or DTHU into 5-formyl-2-furancarboxylic acid (FFA). In some embodiments of method E, the method further includes isolating the FFA.

In some embodiments that may be combined with any of the preceding embodiments of method E, the converting of the DEHU or DTHU into FFA includes dehydrating and cyclizing the DEHU or DTHU. In other embodiments of method E, the converting of the DEHU or DTHU into FFA includes combining the DEHU or DTHU with a catalyst to form a reaction mixture. In some embodiments that may be combined with any of the preceding embodiments of method E, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method E, the catalyst is an inorganic acid, such as phosphoric acid, sulfuric acid, or hydrochloric acid. In one embodiment of method E, the catalyst is sulfuric acid. In yet another embodiment of method E, the catalyst is an ion-exchange resin.

In some embodiments that may be combined with any of the preceding embodiments of method E, the converting of the DEHU or DTHU into FFA is performed neat. In some embodiments of method E, the reaction mixture is combined with a solvent. In certain embodiments of method E, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In some embodiments of method E, the solvent is water or methanol.

In some embodiments that may be combined with any of the preceding embodiments of method E, the converting of the DEHU or DTHU into FFA may further include heating the reaction mixture. In certain embodiments of method E, the reaction mixture is heated to a temperature between 50° C. and 500° C.

In some embodiments of method E, the DEHU is obtained from alginate. In other embodiments of method E, the DTHU is obtained from pectin.

The present disclosure addresses this need by providing methods to produce 2,5-furandicarboxylic acid (FDCA) from seaweed, alginate, oligoalginate, alginate monomers (e.g., mannuronate and guluronate), pectin, oligopectin, polygalacturonate, oligogalacturonate, pectin monomers (e.g., galacturonate), or a combination thereof.

In one aspect, the present disclosure provides a method F of producing 2,5-furandicarboxylic acid (FDCA), by: a) providing seaweed; b) digesting the seaweed to produce a digested seaweed and residual solids, in which the digested seaweed includes one or more sugars; and c) converting the one or more sugars in the digested seaweed into FDCA. In some embodiments of method F, the method further includes isolating the FDCA.

In some embodiments of method F that may be combined with any of the preceding embodiments, the seaweed is red algae, green algae, brown algae, or a combination thereof. In one embodiment of method F, the seaweed is brown algae.

In some embodiments that may be combined with any of the preceding embodiments of method F, the one or more sugars are chosen from glucose, mannitol, and alginate. In other embodiments of method F, the one or more sugars are two or more sugars chosen from glucose, mannitol, and alginate. In other embodiments of method F, the one or more sugars are a mixture of sugars chosen from glucose, mannitol, and alginate.

In other embodiments that may be combined with any of the preceding embodiments of method F, the residual solids include proteins. In yet other embodiments that may be combined with any of the preceding embodiments of method F, the method further includes removing the residual solids from the digested seaweed before converting the one or more sugars in the digested seaweed into FDCA.

In some embodiments that may be combined with any of the preceding embodiments of method F, the seaweed is enzymatically digested. In some embodiments that may be combined with any of the preceding embodiments of method F, the one or more sugars in the digested seaweed are converted into FDCA by dehydration and oxidation. In some embodiments of method F, the dehydration is performed chemically or enzymatically. In some embodiments of method F, the oxidation is performed chemically or enzymatically.

In other embodiments of method F, the converting of the one or more sugars in the digested seaweed into FDCA includes: converting the one or more sugars into one or more intermediates chosen from 5-hydroxymethyl furfural (HMF), 2,5-dihydroxymethyl furan (DHMF), and 5-formyl-2-furancarboxylic acid (FFA); and oxidizing the one or more intermediates into FDCA.

In some embodiments of method F, the one or more intermediates are two or more intermediates chosen from HMF, DHMF, and FFA. In other embodiments of method F, the one or more intermediates are a mixture of intermediates chosen from HMF, DHMF, and FFA.

In some embodiments of method F, the one or more sugars are converted into the one or more intermediates by combining the one or more sugars with a catalyst to form a reaction mixture. In some embodiments of method F, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, and a combination thereof. In other embodiments of method F, the catalyst is an inorganic acid, such as phosphoric acid, sulfuric acid, or hydrochloric acid. In one embodiment of method F, the catalyst is sulfuric acid. In yet another embodiment of method F, the catalyst is an ion-exchange resin.

In some embodiments that may be combined with any of the preceding embodiments of method F, the converting of the one or more sugars into the one or more intermediates is performed neat. In other embodiments of method F, the reaction mixture that includes the one or more sugars and the catalyst is combined with a solvent. In some embodiments of method F, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In certain embodiments of method F, the solvent is water or methanol. In one embodiment of method F, the solvent is water.

In some embodiments that may be combined with any of the preceding embodiments of method F, the converting of the one or more sugars into the one or more intermediates may further include heating the reaction mixture. In certain embodiments of method F, the reaction mixture is heated to a temperature between 50° C. and 500° C.

In some embodiments that may be combined with any of the preceding embodiments of method F, the oxidizing of the one or more intermediates to produce FDCA involves combining the one or more intermediates with an oxidant. The oxidation reaction may be catalyzed or uncatalyzed. In certain embodiments of method F, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method F, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method F, the oxidation catalyst is platinum on carbon. In some embodiments that may be combined with any of the preceding embodiments of method F, the oxidizing of the one or more intermediates to produce FDCA further involves combining the one or more intermediates and the oxidant in water.

In some embodiments of method F, the digested seaweed includes glucose. In some embodiments of method F where the digested seaweed includes glucose, the converting of the glucose in the digested seaweed into FDCA includes: converting the glucose into 5-hydroxymethyl furfural (HMF); and oxidizing the HMF into FDCA. In some embodiments of method F where the digested seaweed includes glucose, the glucose is converted into the HMF by combining the glucose with a catalyst to form a reaction mixture.

In some embodiments of method F where the digested seaweed includes glucose, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, and a combination thereof. In other embodiments of method F where the digested seaweed includes glucose, the catalyst is an inorganic acid, such as phosphoric acid, sulfuric acid, or hydrochloric acid. In one embodiment of method F where the digested seaweed includes glucose, the catalyst is sulfuric acid. In yet another embodiment of method F where the digested seaweed includes glucose, the catalyst is an ion-exchange resin.

In some embodiments of method F where the digested seaweed includes glucose, the converting of the glucose into the HMF is performed neat. In other embodiments of method F where the digested seaweed includes glucose, the reaction mixture that includes the glucose and the catalyst is combined with a solvent. In some embodiments of method F where the digested seaweed includes glucose, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In certain embodiments of method F where the digested seaweed includes glucose, the solvent is water or methanol. In one embodiment of method F where the digested seaweed includes glucose, the solvent is water.

In some embodiments of method F where the digested seaweed includes glucose, the converting of the glucose into the HMF may further include heating the reaction mixture. In certain embodiments of method F where the digested seaweed includes glucose, the reaction mixture is heated to a temperature between 50° C. and 500° C.

In some embodiments of method F where the digested seaweed includes glucose, the oxidizing of the HMF to produce FDCA involves combining the HMF with and an oxidant. In certain embodiments of method F, where the digested seaweed includes glucose, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method F where the digested seaweed includes glucose, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method F where the digested seaweed includes glucose, the oxidation catalyst is platinum on carbon. In some embodiments that may be combined with any of the preceding embodiments of method F where the digested seaweed includes glucose, the oxidizing of the HMF to produce FDCA further involves combining the HMF and the oxidant in water.

In other embodiments of method F, the digested seaweed includes mannitol. In some embodiments of method F where the digested seaweed includes mannitol, the converting of the mannitol in the digested seaweed into FDCA includes: converting the mannitol into 2,5-dihydroxymethyl furan (DHMF); and oxidizing the DHMF into FDCA. In some embodiments of method F where the digested seaweed includes mannitol, the mannitol is converted into the DHMF by combining the mannitol with a catalyst to form a reaction mixture. In some embodiments of method F where the digested seaweed includes mannitol, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, and a combination thereof. In other embodiments of method F where the digested seaweed includes mannitol, the catalyst is an inorganic acid, such as phosphoric acid, sulfuric acid, or hydrochloric acid. In one embodiment of method F where the digested seaweed includes mannitol, the catalyst is sulfuric acid. In yet another embodiment of method F where the digested seaweed includes mannitol, the catalyst is an ion-exchange resin.

In some embodiments of method F where the digested seaweed includes mannitol, the converting of the mannitol into the DHMF is performed neat. In other embodiments of method F where the digested seaweed includes mannitol, the reaction mixture that includes the mannitol and the catalyst is combined with a solvent. In some embodiments of method F where the digested seaweed includes mannitol, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In certain embodiments of method F where the digested seaweed includes mannitol, the solvent is water or methanol. In one embodiment of method F where the digested seaweed includes mannitol, the solvent is water.

In some embodiments of method F where the digested seaweed includes mannitol, the converting of the mannitol into the DHMF may further include heating the reaction mixture. In certain embodiments of method F where the digested seaweed includes mannitol, the reaction mixture is heated to a temperature between 50° C. and 500° C.

In some embodiments of method F where the digested seaweed includes mannitol, the oxidizing of the DHMF to produce FDCA involves combining the DHMF with and an oxidant. In certain embodiments of method F where the digested seaweed includes mannitol, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method F where the digested seaweed includes mannitol, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method F where the digested seaweed includes mannitol, the oxidation catalyst is platinum on carbon. In some embodiments that may be combined with any of the preceding embodiments of method F where the digested seaweed includes mannitol, the oxidizing of the DHMF to produce FDCA further involves combining the DHMF and the oxidant within water.

In other embodiments of method F, the digest seaweed includes alginate. In some embodiments of method F where the digested seaweed includes alginate, the converting of the alginate in the digested seaweed into FDCA includes: converting the alginate into 5-formyl-2-furancarboxylic acid (FFA); and oxidizing the FFA into FDCA. In some embodiments of method F where the digested seaweed includes alginate, the alginate is converted into the FFA by combining the alginate with a catalyst to form a reaction mixture. In some embodiments of method F where the digested seaweed includes alginate, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, and a combination thereof. In other embodiments of method F where the digested seaweed includes alginate, the catalyst is an inorganic acid, such as phosphoric acid, sulfuric acid, or hydrochloric acid. In one embodiment of method F where the digested seaweed includes alginate, the catalyst is sulfuric acid. In yet another embodiment of method F where the digested seaweed includes alginate, the catalyst is an ion-exchange resin.

In some embodiments of method F where the digested seaweed includes alginate, the converting of the alginate into the FFA is performed neat. In other embodiments of method F where the digested seaweed includes alginate, the reaction mixture that includes the alginate and the catalyst is combined with a solvent. In some embodiments of method F where the digested seaweed includes alginate, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In certain embodiments of method F where the digested seaweed includes alginate, the solvent is water or methanol. In one embodiment of method F where the digested seaweed includes alginate, the solvent is water.

In some embodiments of method F where the digested seaweed includes alginate, the converting of the alginate into the FFA may further include heating the reaction mixture. In certain embodiments of method F where the digested seaweed includes alginate, the reaction mixture is heated to a temperature between 50° C. and 500° C.

In some embodiments of method F where the digested seaweed includes alginate, the oxidizing of the FFA to produce FDCA involves combining the FFA with and an oxidant. In certain embodiments of method F where the digested seaweed includes alginate, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method F where the digested seaweed includes alginate, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method F where the digested seaweed includes alginate, the oxidation catalyst is platinum on carbon. In some embodiments that may be combined with any of the preceding embodiments of method F where the digested seaweed includes alginate, the oxidizing of the FFA to produce FDCA further involves combining the FFA and the oxidant in water.

In some embodiments that may be combined with any of the preceding embodiments of method F, the method yields at least 20% of the theoretical maximum of FDCA that may be produced from the seaweed. In other embodiments that may be combined with any of the preceding embodiments of method F, the method further includes harvesting the seaweed. In yet other embodiments that may be combined with any of the preceding embodiments of method F, the FDCA is used as a precursor for producing adipic acid.

In another aspect, the present disclosure provides a method G of producing 2,5-furandicarboxylic acid (FDCA), by: a) providing a starting material chosen from alginate, oligoalginate, a monomer alginate (e.g., mannuronate and guluronate), pectin, oligopectin, polygalacturonate, galacturonate, oligogalacturonate, or a combination thereof; b) converting the starting material into 5-formyl-2-furancarboxylic acid (FFA); and c) oxidizing the FFA to produce FDCA. In some embodiments of method G, the method further includes isolating the FDCA.

In some embodiments of method G, the starting material is alginate, oligoalginate, and/or alginate monomers (e.g., mannuronate and guluronate). In one embodiment of method G, the starting material is alginate. In another embodiment of method G, the alginate, oligoalginate, or a combination thereof is obtained from seaweed. In yet other embodiments of method G, the alginate, oligoalginate, alginate monomers (e.g., mannuronate and guluronate), or a combination thereof may be obtained from seaweed.

In some embodiments that may be combined with any of the preceding embodiments of method G, the starting material (e.g., alginate, oligoalginate, pectin, oligopectin, polygalacturonate, galacturonate, and/or oligogalacturonate) is converted into FFA by combining the starting material with a catalyst to form a reaction mixture. In some embodiments that may be combined with any of the preceding embodiments of method G, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method G, the catalyst is an inorganic acid, such as phosphoric acid, sulfuric acid, or hydrochloric acid. In one embodiment of method G, the catalyst is sulfuric acid. In yet another embodiment of method G, the catalyst is an ion-exchange resin.

In some embodiments that may be combined with any of the preceding embodiments of method G, the converting of the starting material into FFA is performed neat. In other embodiments of method G, the reaction mixture that includes the starting material and the catalyst is combined with a solvent. In certain embodiments of method G, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In some embodiments of method G, the solvent is water or methanol. In one embodiment of method G, the solvent is water.

In some embodiments that may be combined with any of the preceding embodiments of method G, the converting of the starting materials into FFA may further include heating the reaction mixture. In certain embodiments of method G, the reaction mixture is heated to a temperature between 50° C. and 500° C.

In some embodiments that may be combined with any of the preceding embodiments of method G, the oxidizing of the FFA to produce FDCA involves combining the FFA with an oxidant. The oxidation reaction may be catalyzed or uncatalyzed. In certain embodiments of method G, the oxidant is bromine, nitric acid, or a peroxide. Optionally, an oxidant such as oxygen or air may be combined with a catalyst to facilitate the oxidation. Suitable oxidation catalysts may include, for example, platinum, gold, palladium, rhodium, copper, molybdenum, vanadium, titanium, cobalt, nickel, iron or a combination thereof. In some embodiments of method G, the oxidation catalyst may be supported. For example, the oxidation catalyst can be platinum on a solid support, such as platinum on carbon, platinum on silica, platinum on titanium dioxide, or platinum on alumina. Suitable supports include, for example, silica, titanium dioxide, alumina, silica alumina, and carbon. In one embodiment of method G, the oxidation catalyst is platinum on carbon. In some embodiments that may be combined with any of the preceding embodiments of method G, the oxidizing of the one or more intermediates to produce FDCA further involves combining the one or more intermediates and the oxidant in water.

In some embodiments that may be combined with any of the preceding embodiments of method G, the method yields at least 20% of the theoretical maximum of FDCA that may be produced from the seaweed. In other embodiments that may be combined with any of the preceding embodiments of method G, the method further includes harvesting the seaweed. In yet other embodiments that may be combined with any of the preceding embodiments of method G, the FDCA is used as a precursor for producing adipic acid.

In some of the foregoing embodiments, the methods are carried out in a single reaction vessel. In other embodiments, the reaction intermediates are used in the next step of the process without isolation or purification. In yet other embodiments, the reaction steps are carried out using a continuous flow reactor. In alternative embodiments, certain reaction intermediates (e.g. FFA) are isolated prior to the next reaction.

In another aspect, the present disclosure provides a method H of producing 5-formyl-2-furancarboxylic acid (FFA), by: a) providing a starting material chosen from alginate, oligoalginate, alginate monomers (e.g., mannuronate and guluronate), pectin, oligopectin, polygalacturonate, galacturonate, oligogalacturonate, and a combination thereof; b) converting the starting material into 5-formyl-2-furancarboxylic acid (FFA); and c) isolating the FFA.

In some embodiments that may be combined with any of the preceding embodiments of method H, the converting of the starting material into FFA includes dehydrating and cyclizing the starting material. In other embodiments of method H, the converting of the starting material into FFA includes combining the starting material with a catalyst to form a reaction mixture. In some embodiments that may be combined with any of the preceding embodiments of method H, the catalyst is oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, or a combination thereof. In other embodiments of method H, the catalyst is an inorganic acid, such as phosphoric acid, sulfuric acid, or hydrochloric acid. In one embodiment of method H, the catalyst is sulfuric acid. In yet another embodiment of method H, the catalyst is an ion-exchange resin.

In some embodiments that may be combined with any of the preceding embodiments of method H, the converting of the starting material into FFA is performed neat. In some embodiments of method H, the reaction mixture is combined with a solvent. In certain embodiments of method H, the solvent is a C1-C20 alcohol. In other embodiments, the solvent is water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, or a combination thereof. In some embodiments of method H, the solvent is water or methanol.

In some embodiments that may be combined with any of the preceding embodiments of method H, the converting of the starting material into FFA may further include heating the reaction mixture. In certain embodiments of method H, the reaction mixture is heated to a temperature between 50° C. and 500° C.

In yet another aspect, the present disclosure provides a method I of producing a compound of Formula (II), by: a) providing 4-deoxy-L-erythro-5-hexoseulose uronate (DEHU); b) oxidizing the DEHU to produce 2,3-dihydroxy-5-oxohexanedioic acid (DOHA); and c) converting the DOHA into a compound of Formula (II),

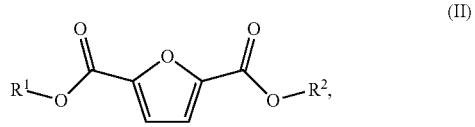

(II)

wherein $R^1$ and $R^2$ are each independently H or $C_{1-20}$ alkyl, in the presence of a solvent, wherein the solvent is an alkyl alcohol, In some embodiments, $R^1$ and $R^2$ are both H. In other embodiments, $R^1$ is H, and $R^2$ is $C_{1-20}$ alkyl. In other embodiments, $R^1$ and $R^2$ are both $C_{1-20}$ alkyl.

In some embodiments, the solvent is selected from methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol. In one embodiment where the solvent is ethanol, $R^1$ is H or ethyl, and $R^2$ is ethyl.

In some embodiments, the oxidizing of DEHU to produce DOHA includes combining DEHU with an oxidant. In certain embodiments, the oxidant is bromine, nitric acid, peroxide, a platinum catalyst, a gold catalyst, a palladium catalyst, a rhodium catalyst, a copper catalyst, a molybdenum catalyst, a vanadium catalyst, a titanium catalyst, a cobalt catalyst, a nickel catalyst, an iron catalyst, and a combination thereof. In one embodiment, the oxidant is platinum on a solid support. In another embodiment, the oxidant is platinum on carbon, platinum on silica, platinum on titanium dioxide, or platinum on alumina. In other embodiments, the oxidizing of DEHU to produce DOHA further comprises combining the DEHU and the oxidant with water.

In some embodiments, the converting of the DOHA into the compound of Formula (II) comprises dehydrating and cyclizing the DOHA. In certain embodiments, the converting of the DOHA into the compound of Formula (II) comprises combining DOHA with a catalyst to form a reaction mixture. In certain embodiments, the catalyst is selected from oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, and a combination thereof.

In some embodiments, the dehydrating and cyclizing of DOHA further includes heating the reaction mixture. In some embodiments, the reaction mixture is heated to a temperature between 50° C. and 500° C. In other embodiments, the DEHU is obtained from alginate. In yet other embodiments, the method yields at least 20% of the theoretical maximum of FDCA that may be produced from DEHU. In yet other embodiments, the FDCA serves as a precursor for producing adipic acid.

DESCRIPTION OF THE FIGURES

The present application can be best understood by reference to the following description taken in conjunction with the accompanying drawing figures, in which like parts may be referred to by like numerals:

FIG. 22A) into DOHA (m/z⁻=191: FIG. 22B). The dotted line depicts time at 0 min and the solid line depicts time at 334 min after the oxidation reaction started;

DETAILED DESCRIPTION

The following description sets forth exemplary methods, parameters and the like. It should be recognized, however, that such description is not intended as a limitation on the scope of the present disclosure but is instead provided as a description of exemplary embodiments.

The following description relates to various methods for synthesizing 2,5-furandicarboxylic acid (FDCA). In one aspect, provided is a method for synthesizing FDCA from intermediates such as DEHU or DTHU.

Figure 1:
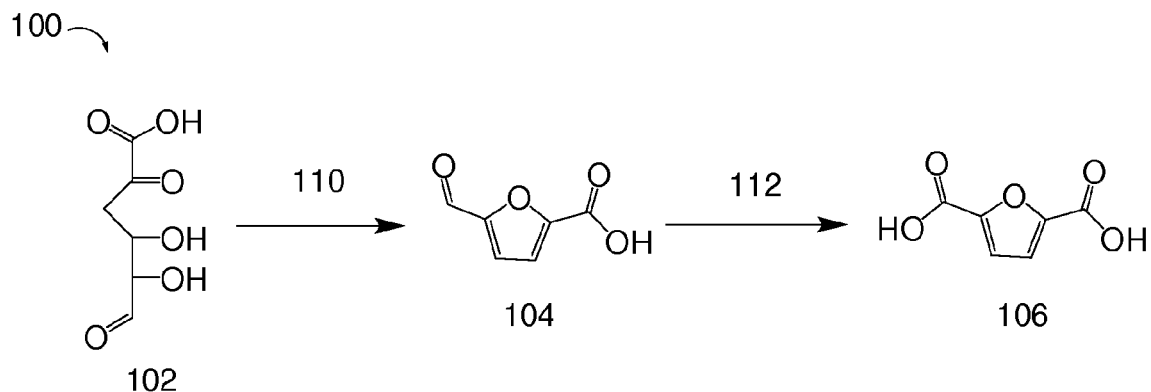
FIG. 1 is an exemplary reaction scheme depicting the conversion of DEHU by dehydration and cyclization, followed by oxidation to produce FDCA.

With reference to FIG. 1, reaction 100 is an exemplary embodiment that depicts dehydrating and cyclizing DEHU before oxidation into FDCA. DEHU 102 is first converted into 5-formyl-2-furancarboxylic acid (FFA) 104 in step 110, which involves the dehydration and cyclization of DEHU. Step 110 may be carried out by any suitable methods known in the art, including for example catalysis by organic acids, inorganic acids, salts, Lewis acids, or solid acid catalysts. With reference again to FIG. 1, FFA 104 is then oxidized in step 112 to produce FDCA 106. Oxidation step 112 may be carried out by any suitable methods known in the art. For example, the oxidation of FFA may be carried out using bromine, nitric acid, TEMPO-like nitroxide oxidation catalysts, peroxide, or catalysts containing platinum, gold, palladium, rhodium, copper, molybdenum, vanadium, titanium, cobalt, nickel, or iron.

Figure 2:
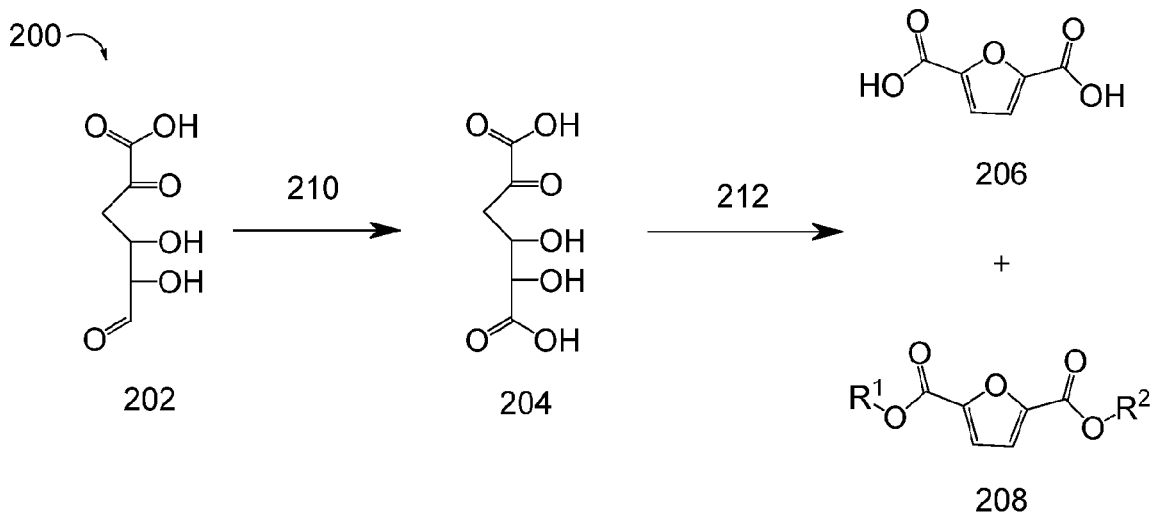
FIG. 2 is an exemplary reaction scheme depicting the conversion of DEHU by oxidation, followed by dehydration and cyclization to produce FDCA and FDCA esters.

With reference to FIG. 2, reaction 200 is an exemplary embodiment that depicts oxidizing DEHU before dehydration and cyclization into FDCA. DEHU 202 is first converted into (2S)-DOHA 204 in step 210, which involves the oxidation of DEHU. Step 210 may be carried out by any suitable methods known in the art, including for example, using bromine, nitric acid, TEMPO-like nitroxide oxidation catalysts, peroxide, or catalysts containing platinum, gold, palladium, rhodium, copper, molybdenum, vanadium, titanium, cobalt, nickel, or iron.

With reference again to FIG. 2, (2S)-DOHA 204 may be converted in step 212 to produce FDCA 206 and/or FDCA ester 208 by dehydration and cyclization, depending on the solvent and reaction conditions used. Step 212 may be carried out by any suitable methods known in the art, including for example catalysis by organic acids, inorganic acids, salts, Lewis acids, or solid acid catalysts. In certain embodiments where an alkyl solvent is used in step 212, it should be understood that FDCA ester 208 may be formed. For example, when ethanol is used as the solvent, FDCA ester 208 may be 5-(ethoxycarbonyl)furan-2-carboxylic acid (a monoester) or diethyl furan-2,5-dicarboxylate (a diester). It should also be understood that the type of FDCA ester formed will depend on the alkyl substituent of the alcohol solvent. Further, it should also be understood that, in some embodiments, a mixture of FDCA 206 and FDCA ester 208 may be formed depending on the reaction conditions. In other embodiments, FDCA 206 is primarily formed. In yet other embodiments, FDCA ester 208 is primarily formed.

Figure 3:
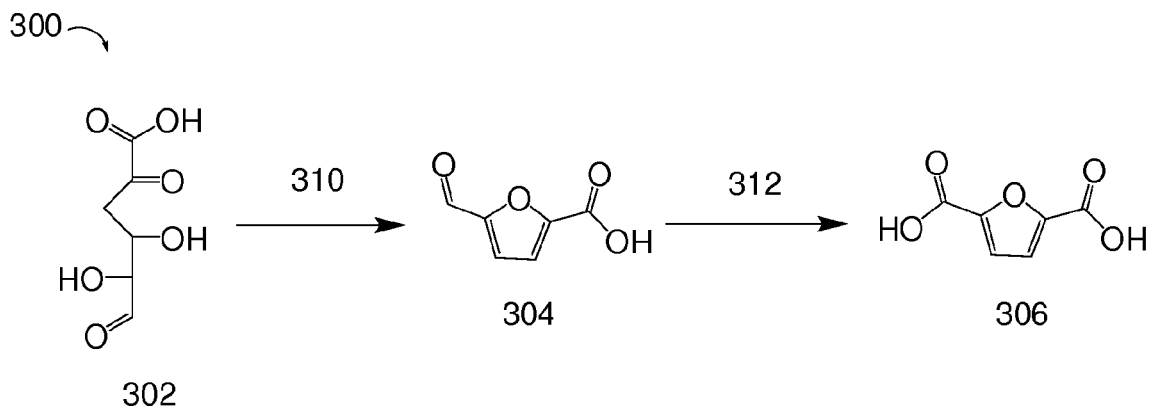
FIG. 3 is an exemplary reaction scheme depicting the conversion of DTHU by dehydration and cyclization, followed by oxidation to produce FDCA.

With reference to FIG. 3, reaction 300 is an exemplary embodiment that depicts dehydrating and cyclizing DTHU before oxidation into FDCA. DTHU 302 is first converted into 5-formyl-2-furancarboxylic acid (FFA) 304 in step 310, which involves the dehydration and cyclization of DTHU. Step 310 may be carried out by any suitable methods known in the art, including for example catalysis by organic acids, inorganic acids, salts, Lewis acids, or solid acid catalysts. With reference again to FIG. 3, FFA 304 is then oxidized in step 312 to produce FDCA 306. Oxidation step 312 may be carried out by any suitable methods known in the art. For example, the oxidation of FFA may be carried out using bromine, nitric acid, TEMPO-like nitroxide oxidation catalysts, peroxide, or catalysts containing platinum, gold, palladium, rhodium, copper, molybdenum, vanadium, titanium, cobalt, nickel, or iron.

Figure 4:
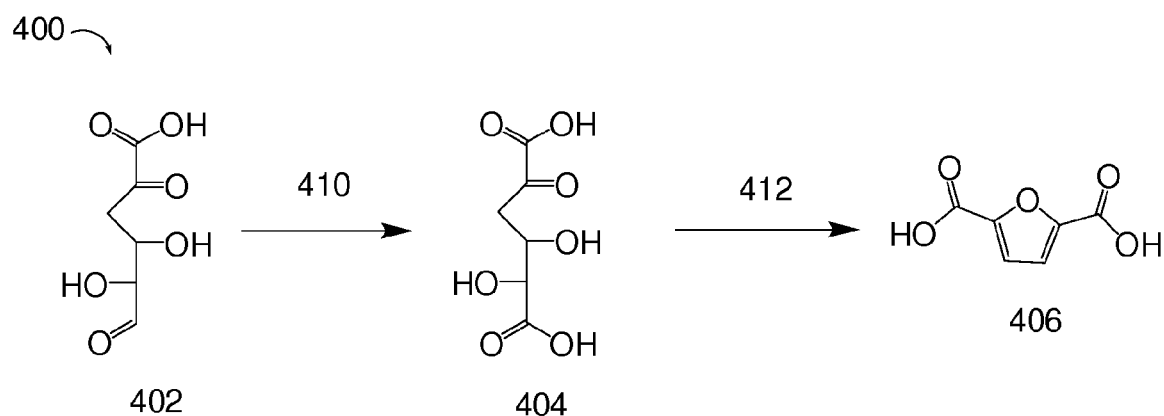
FIG. 4 is an exemplary reaction scheme depicting the conversion of DTHU by oxidation, followed by dehydration and cyclization to produce FDCA.

With reference to FIG. 4, reaction 400 is an exemplary embodiment that depicts oxidizing DTHU before dehydration and cyclization into FDCA. DTHU 402 is first converted into (2R)-DOHA 404 in step 410, which involves the oxidation of DTHU. Step 410 may be carried out by any suitable methods known in the art, including for example, using bromine, nitric acid, TEMPO-like nitroxide oxidation catalysts, peroxide, or catalysts containing platinum, gold, palladium, rhodium, copper, molybdenum, vanadium, titanium, cobalt, nickel, or iron. With reference again to FIG. 4, (2R)-DOHA 404 is then converted in step 412 to produce FDCA 406 by dehydration and cyclization. Step 412 may be carried out by any suitable methods known in the art, including for example catalysis by organic acids, inorganic acids, salts, lewis acids, or solid acid catalysts.

It should be noted, however, that reactions 100, 200, 300 and 400 may involve additional steps. For example, in one embodiment, reaction 100 may involve isolating FFA 104 before step 112. Similarly, in another embodiment, reaction 200 may involve isolating (2S)-DOHA 204 before step 212. In another embodiment, reaction 300 may involve isolating FFA 304 before step 312. Similarly, in another embodiment, reaction 400 may involve isolating (2R)-DOHA 404 before step 412.

The methods described above may also be performed as a "one-pot" reaction. In one embodiment, for instance, FFA 104 formed in the step 110 of reaction 100 is not isolated from the reaction mixture or purified before performing step 112. Similarly, in another embodiment, (2S)-DOHA 204 formed in step 210 of reaction 200 is not isolated from the reaction mixture or purified before performing step 212. In another embodiment, FFA 304 formed in the step 310 of reaction 300 is not isolated from the reaction mixture or purified before performing step 312. Similarly, in another embodiment, (2R)-DOHA 404 formed in step 410 of reaction 400 is not isolated from the reaction mixture or purified before performing step 412.

In another aspect, provided is a method for synthesizing FDCA from intermediates, such as HMF, DHMF or FFA.

Figure 13:
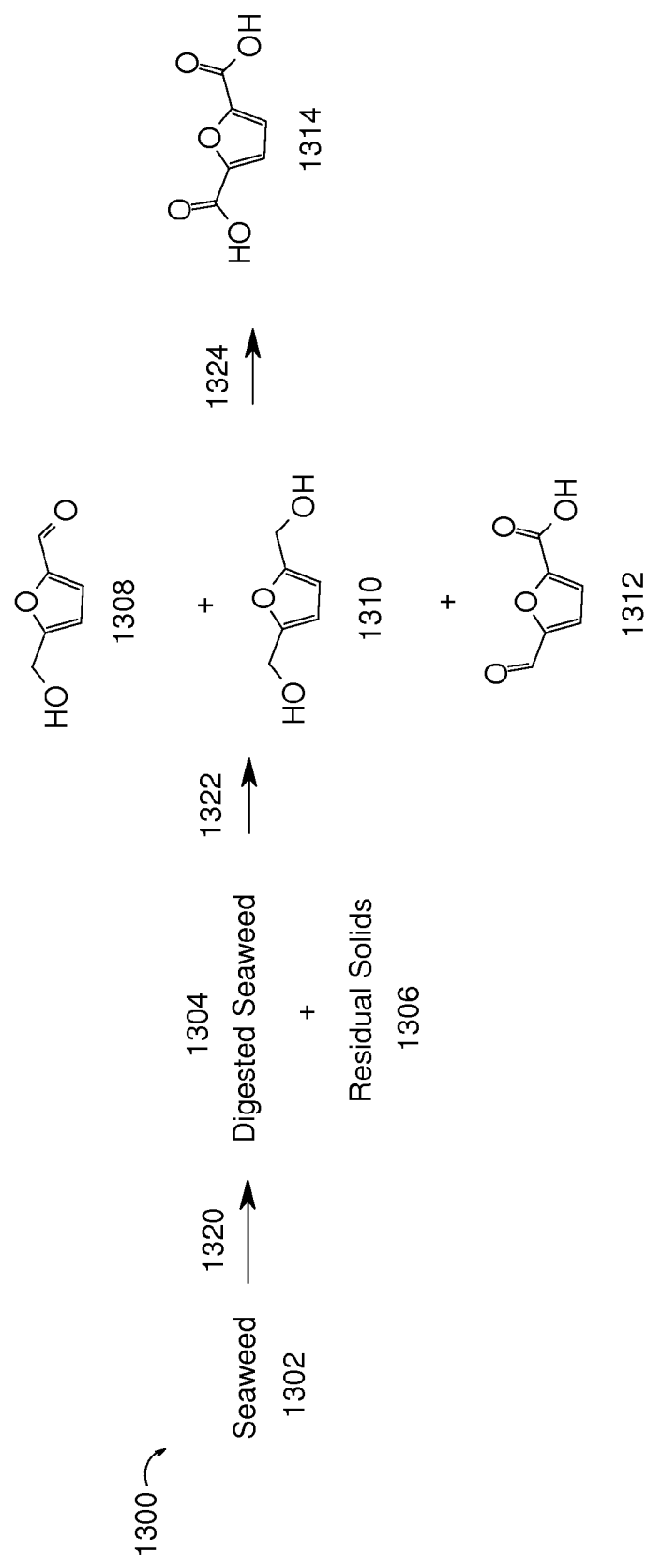
FIG. 13 is an exemplary reaction scheme depicting the conversion of seaweed into FDCA.

With reference to FIG. 13, reaction 1300 is an exemplary embodiment that depicts the synthesis of FDCA from seaweed. Seaweed 1302 is first chemically or enzymatically digested in step 1320 to produce digested seaweed 1304 and residual solids 1306. Step 1320 may be carried out by any suitable enzymes known in the art, including enzymes obtained from a recombinant source. Digested seaweed 1304 contains a mixture of sugars, such as glucose, mannitol, and alginate, which are soluble in the reaction mixture.

It should be understood that in other exemplary embodiments, seaweed 1302 may be chemically digested to produce digested seaweed and residual solids.

It should be also understood that, in other exemplary embodiments, the composition of digested seaweed 1304 may vary. While digested seaweed 1304 includes a mixture of glucose, mannitol and alginate, in other exemplary embodiments, the digested seaweed may include glucose and mannitol, or glucose and alginate, or mannitol and alginate, or one of glucose, mannitol or alginate. The relative amounts of glucose, mannitol and/or alginate present in digested seaweed 1304 may also vary.

Residual solids 1306 may include residual proteins, including those residual proteins that have low solubility in the reaction mixture. Digested seaweed 1304 may be separated from residual solids 1306 and isolated by any methods known in the art (e.g., filtration), prior to conversion into FDCA. The sugars in digested seaweed 1304 are converted into a mixture of intermediates: 5-hydroxymethyl furfural (HMF) 1308, 2,5-dihydroxymethyl furan (DHMF) 1310, and 5-formyl-2-furancarboxylic acid (FFA) 1312.

It should be understood, however, that the intermediates present in the reaction mixture may depend on the composition of digested seaweed 1304. Glucose is typically converted into HMF, whereas mannitol is typically converted into DHMF and alginate into FFA. While the mixture of intermediates in reaction 1300 includes a mixture of HMF, DHMF and FFA, in other exemplary embodiments, the mixture of intermediates may include HMF and DHMF, or DHMF and FFA, or DHMF and FFA, or one of HMF, DHMF or FFA. The relative amounts of HMF, DHMF and/or FFA produced from the digested seaweed may also vary.

In step 1324, intermediates 1308, 1310 and 1312 are converted into FDCA 1314 via one or more reactions, including acid-catalyzed dehydration and oxidation.

Figure 14:
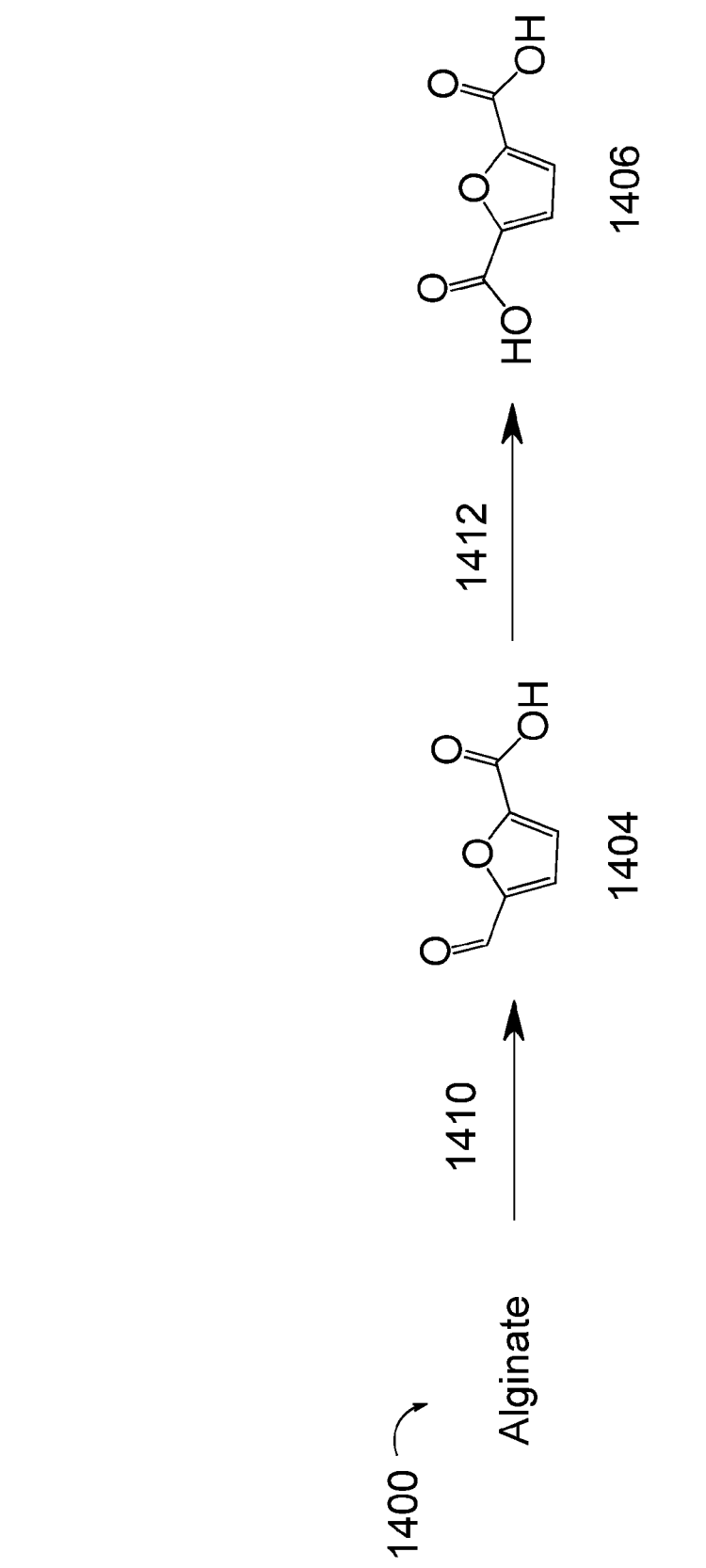
FIG. 14 is an exemplary reaction scheme depicting the conversion of alginate into FDCA.

With reference to FIG. 14, reaction 1400 is an exemplary embodiment that depicts the synthesis of FDCA from alginate. Alginate 1402 is first converted into 5-formyl-2-furancarboxylic acid (FFA) 1404 in step 1410. The β-D-mannuronate and/or α-L-guluronate in the alginate are converted into FFA in the presence of a catalyst. In some embodiments, the reaction may be performed neat, or with a solvent. FFA 1404 is then oxidized in step 1412 to produce FDCA 1406. Oxidation step 1412 may be carried out by any suitable methods known in the art. For example, the oxidation of FFA may be carried out using bromine, nitric acid, TEMPO-like nitroxide oxidation catalysts, peroxide, or catalysts containing platinum, gold, palladium, rhodium, copper, molybdenum, vanadium, titanium, cobalt, nickel, or iron.

Although the starting material in FIG. 14 is alginate, in other exemplary embodiments, the starting material may be oligoalginate, pectin, oligopectin, polygalacturonate, galacturonate, oligogalacturonate, or a combination of these starting materials.

It should be noted that reactions 1300 and 1400 may involve additional steps. For example, in one embodiment, reaction 1300 may involve separating the mixture of sugars in digested seaweed 1304 before one or more separated sugars is converted to FDCA in step 1312. Similarly, in another embodiment, reaction 1400 may involve isolating FFA 1404 before step 1412.

The disclosed methods may also be performed as a "one-pot" reaction. In one embodiment, for instance, digested seaweed 1304 formed in the step 1320 of reaction 1300 is not isolated from the reaction mixture before performing step 1322. Similarly, in another embodiment, FFA 1404 formed in step 1410 of reaction 1400 is not isolated from the reaction mixture or purified before performing step 1412.

The methods to produce FDCA described above involve various components, and reaction conditions, which are each described in more detail below.

Feedstock

Seaweed, alginate, oligoalginate, alginate monomers (e.g., mannuronate and guluronate), pectin, oligopectin, polygalacturonate, galacturonate, and/or oligogalacturonate can be used as starting materials in the methods described herein to produce FDCA.

a) Seaweed

Seaweed may include red algae, brown algae, or green algae. Red algae typically have cellulose and galactose. Brown algae typically have alginate, mannitol, cellulose, and laminarin. Green algae typically have cellulose and pectin. In some embodiments, the seaweed used in the methods described herein may be any one of these forms of algae, or a combination thereof. In a certain embodiment, the seaweed includes brown algae.

Examples of suitable brown algae may include kelp, giant kelp, sargasso, seaweed, *Laminaria japonica, Undaria pinnatifida, Hizikia fusiforme, Analipus japonicus, Chordaria flagelliformis, Ishige okamurai, Scytosiphon lomentaria, Endarachne binghamiae, Ecklonia cava, Ecklonia stolonifera, Eisenia bicyclis, Costaria costata, Sargassum fulvellum, Sargassum horneri, Sargassum thunbergii, Saccharina latissima, Saccharina digitata, Macrocystis* sp., and *Macrocystis pyrifera*.

Examples of suitable green algae may include *Enteromorpha, Spirogyra* spp., *Codium fragile, Codium minus, Caulerpa okamurai*, and *Nostoc com.mune*.

Examples of suitable red algae may include *Gelidium amansii, Gracilaria verrucosa, Bangia atropurpurea, Porphyra suborbiculata, Porphyra yezoensis, Galaxaura falcate, Scinaia japonica, Gelidium divaricatum, Gelidium pacificum, Lithophylum okamurae, Lithothammion cystocarpideum, Amphiroa anceps, Amphiroa beauvoisii, Corallina officinalis, Corallina pilulifera, Marginisporum aberrans,*

*Carpopeltis prolifera, Grateloupia filicina, Grateloupia elliptica, Grateloupia lanceolanta, Grateloupia turtuturu, Phacelocarpus japonicus, Gloiopeltis furcata, Hypnea charoides, Hypnea japonitca, Hypnea saidana, Chondrus cripspus, Chondracanthus tenellus, Gracilaria textorii, Lomentaria catenata, Heterosiphonia japonica, Chondria crassicaulis, Symphyocladia latiuscula, Porphyra yezoensis Ueda, Eucheuma Cottonii, Grateloupia lanceolata, Pterocladia tenuis, Acanthopeltis japonica, Gloiopeltis tenax, Irish moss, Pachymeniopsis elliptica, Ceramium kondoi, Ceramium boydenii, Gigartina tenella,* and *Campylaephora hypnaeoides.*

Prior to using the seaweed in reaction 1300, the seaweed may be pre-treated to improve reactivity in the methods described herein.

b) Alginate and Oligoalginate

Alginate is a polysaccharide found in the cell walls of seaweed, in particular, brown algae. Alginate is a linear copolymer with homopolymeric blocks of (1-4)-linked β-D-mannuronate (M) and its C-5 epimer α-L-guluronate (G) residues, respectively, covalently linked together in different sequences or blocks. Alginate monomers may appear in homopolymeric blocks of consecutive G-residues (G-blocks), consecutive M-residues (M-blocks), alternating M- and G-residues (MG-blocks), or randomly organized blocks.

The alginate used in reaction 1400 may be obtained from any source known to one skilled in the art. Suitable sources of alginate may include kelp, giant kelp, sargasso, seaweed, algae, brown algae, marine microflora, microalgae, and sea grass.

In some embodiments, alginate may also be chemically or enzymatically degraded to form oligoalginate, which may also be used as a starting material for the methods described herein.

c) Pectin, Oligopectin, Galacturonate, Polygalacturonate, and Oligogalacturonate Pectin is made up of a complex set of polysaccharides that include 1,4-linked α-D-galacturonate. Pectin is typically found in the cell walls of plants, and may be extracted from a variety of sources, including fruits such as orange peels, grapefruit peels, apple peels, and sugar beets.

In some embodiments, pectin may be chemically or enzymatically degraded to form oligopectin, galacturonate, polygalacturonate, or oligogalacturonate, which may also be used as a starting material for the methods described herein.
Intermediates a) DEHU and DTHU Starting materials such as alginate and pectin can be converted into a compound of Formula (I),

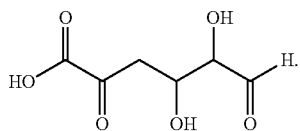

(I)

The compound of Formula (I) may include 4-deoxy-L-erythro-5-hexoseulose uronate (DEHU), 4-deoxy-L-threo-5-hexosulose uronate (DTHU), or a mixture thereof. DEHU and DTHU are diastereomers, and may be obtained from any source and any methods known in the art. In some embodiments, DEHU may be obtained from a renewable source such as alginate. In some embodiments, DTHU may be obtained from a renewable source such as pectin.

DEHU from Alginate

Figure 5:
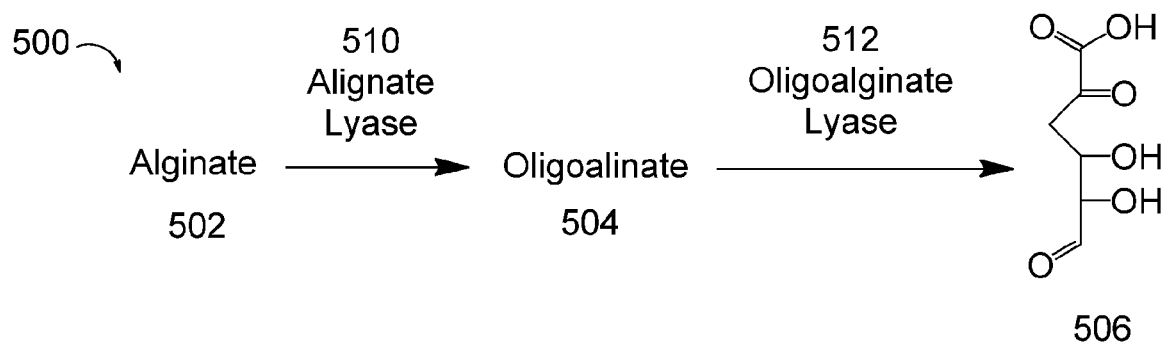
FIG. 5 is an exemplary reaction scheme for producing DEHU from alginate.

DEHU may be obtained from alginate by any chemical or biological methods known in the art. With reference to FIG. 5, in one exemplary embodiment, DEHU may be enzymatically obtained from alginate 502. Alginate is a linear copolymer with homopolymeric blocks of (1-4)-linked β-D-mannuronate (M) and its C-5 epimer α-L-guluronate (G) residues, respectively, covalently linked together in different sequences or blocks. Alginate monomers may appear in homopolymeric blocks of consecutive G-residues (G-blocks), consecutive M-residues (M-blocks), alternating M- and G-residues (MG-blocks), or randomly organized blocks. The alginate may be obtained from any source known to one skilled in the art. Suitable sources of alginate may include kelp, giant kelp, sargasso, seaweed, algae, brown algae, marine microflora, microalgae, and sea grass.

With reference again to FIG. 5, alginate 502 is converted into DEHU using two enzymes: an alginate lyase and an oligoalginate lyase. Alginate lyase 510 breaks down alginate 502 into oligoalginate 504, which may include alginate dimers, trimers, and tetramers. Alginate lyase 510 may be any enzyme that can depolymerize alginate 502 into oligosaccharides, such as disaccharides, trisaccharides, and tetrasaccharides. Suitable alginate lyases may include, for example, polymannuronate lyases, polyguluronate lyases, polygalacturonate lyases, and hyaluronan lyases. Alginate lyases may be isolated from various sources, including marine algae, mollusks, and a wide variety of microbes such as genus *Pseudomonas, Pseudoalteromonas, Vibrio,* and *Sphingomonas.* Alginate lyases may also be obtained from a recombinant source.

With reference again to FIG. 5, oligoalginate lyase 512 may then be added to the reaction mixture to break down the dimers, trimers, and tetramers into DEHU 506. Examples of suitable oligoalginate lyases may include, for example, guluronate lyases. Oligoalginate lyases may also be obtained from a recombinant source.

DTHU from Pectin

DTHU may be obtained from pectin by any chemical or biological methods known in the art. In some embodiments, DTHU may be enzymatically obtained from pectin. Pectin is made up of a complex set of polysaccharides that include 1,4-linked α-D-galacturonate. Pectin is typically found in the cell walls of plants, and may be extracted from a variety of sources, including fruits such as orange peels, grapefruit peels, apple peels, and sugar beets.

b) DMF, DHMF and FFA

HMF, DHMF and FFA may be obtained from any source and any methods known in the art. In some embodiments, these intermediates may be obtained from a renewable source such the sugars in digested seaweed.

Dehydration and Cyclization Reactions

The dehydration and cyclization step described herein may be carried out using any suitable methods or techniques known in the art. The starting materials described herein, including seaweed, alginate, oligoalginate, alginate monomers (e.g., mannuronate and guluronate), pectin, oligopectin, polygalacturonate, galacturonate, and/or oligogalacturonate, may be converted into one or more of the intermediates described above by dehydration and ring opening, followed by the cyclization.

For example, in one embodiment, DEHU undergoes acid-catalyzed dehydration and then cyclizes to form FFA. In another embodiment, DTHU undergoes acid-catalyzed dehydration and then cyclizes to form FFA. In other embodiments, DOHA undergoes acid-catalyzed dehydration and then cyclizes to form FDCA.

In other embodiments, glucose in seaweed is converted into HMF. In yet other embodiments, mannitol in seaweed is converted into DHMF. In yet other embodiments, alginate in seaweed is converted into FFA. In yet other embodiments, the alginate, oligoalginate, alginate monomers (e.g., mannuronate and guluronate), pectin, oligopectin, polygalacturonate, galacturonate, and/or oligogalacturonate are converted into FFA It should be understood that, in some embodiments, the FFA produced from the dehydration and cyclization step can be isolated. The FFA produced may be used to prepare other compounds, for example, FDCA.

a) Catalysts

The dehydration reaction may be carried out using any suitable acid catalysts. The catalyst may be a Lewis acid or a Bronsted acid. Suitable Lewis acids may include, for example, zinc chloride, aluminum chloride, and boron trifluoride. Suitable Bronsted acids may include, for example, hydrochloric acid, hydrofluoric acid, hydrobromic acid, and hydroiodic acid.

In other embodiments, the catalyst may be an organic acid or an inorganic acid. Suitable organic acids may include, for example, oxalic acid, levulinic acid, maleic acid, p-toluenesulfonic acid, Nafion® (tetrafluoroethylene-perfluoro-3,6-dioxa-4-methyl-7-octenesulfonic acid copolymer), SAC-13® (a silica nanocomposite solid acid catalyst), chloro acetic acid, bromo acetic acid, fluoro acetic acid, and citric acid. Suitable inorganic acids may include, for example, phosphoric acid, sulfuric acid, perchloric acid, nitric acid, hydrochloric acid, hydrofluoric acid, hydrobromic acid, and hydroiodic acid.

In yet other embodiments, the catalyst may be a salt. Suitable salts may include, for example, an ammonium salt (e.g., ammonium sulfate, ammonium phosphate), a triethylamine salt (e.g., triethylamine sulfate, triethylamine phosphate), a pyridinium salt (e.g., pyridinium sulfate, pyridinium phosphate, poly-4-vinylpyridinium hydrochloride, pyridinium trifluoroacetate, pyridinium hydrochloride, pyridinium hydrobromide, pyridinium perbromate, pyridinium p-toluenesulfonate), an aluminum salt (e.g., aluminum sulfate, aluminum phosphate), a thorium salt, a zirconium salt (e.g., zirconium phosphate, zirconyl chloride), a vanadium salt, a chromium salt (e.g., chromium trichloride), a zinc salt (e.g., zinc chloride), and a titanium salt.

In yet other embodiments, the catalyst is an acid catalyst, which may be used in solid form. A solid acid catalyst may include a solid material which has been functionalized to impart acid groups that are catalytically active. Solid acid catalysts may have a broad range of composition, porosity, density, type of acid groups, and distribution of acid groups. Solid acid catalysts may be recovered and reused, optionally with a treatment to regenerate any activity that may have been lost in use. Suitable solid acid catalysts may include, for example, an ion-exchange resin, a zeolite, tungstated zirconia, sulfated zirconia, gamma alumina, supported phosphoric acid, or activated carbon. Any combinations of acid catalysts described herein may also be used.

The concentration of the catalyst used in the reaction may vary depending on the nature of the catalyst and the starting materials used. For example, in one embodiment where sulfuric acid is the catalyst, the catalyst has a concentration of at least 5M, 10M, or 15M. In other embodiments where sulfuric acid is the catalyst, the sulfuric acid has a concentration of between 10M and 20M, or between 15M to 18M.

b) Solvents

In some embodiments, the reaction may be performed neat. In other embodiments, a solvent is used in the reaction. A suitable solvent is one where the starting material is fairly soluble, where the solvent does not interfere with the dehydration and cyclization reactions, and is stable at the reaction conditions. A suitable solvent may also promote reaction rate and formation of the reaction product, or reduce the formation of side products.

In some embodiments, the reaction may be carried out in an aqueous solvent, a non-aqueous solvent, or a mixture thereof. In one embodiment, the solvent is water. In yet other embodiments, suitable non-aqueous solvents may include, for example, a C1-C20 alcohol. In certain embodiments, the solvent is methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, dimethylformamide, polyethylene glycol, and methyl isobutyl ketone.

c) Reaction Conditions

The reaction time and temperature of the dehydration and cyclization reactions may vary depending on the starting materials, catalysts and solvents used.

A reaction mixture containing one or more of the intermediates described above may be heated to a temperature sufficient to form FFA. For example, in one embodiment, the reaction mixture containing DEHU may be heated to a temperature sufficient to form FFA. In another embodiment, the reaction mixture containing DTHU may be heated to a temperature sufficient to form FFA. In yet another embodiment, the reaction mixture containing DOHA may be heated to a temperature sufficient to form FDCA.

In some embodiments, the reaction mixtures described herein may be heated to reflux. In other embodiments, the reaction mixture may be heated to between 50° C. and 500° C., between 50° C. and 300° C., between 65° C. and 75° C., between 75° C. and 250° C., or between 100° C. and 175° C. In some embodiments, the reaction mixture may be performed at room temperature. In other embodiments, the reaction may be performed using microwave energy.

In some embodiments, the reaction time may be less than 1 minute, between 5-10 minutes, about 1 hour, about 5 hours, about 24 hours, about 48 hours, between 1-72 hours, between 1-24 hours, between 1-10 hours, or between 1-5 hours.

Oxidation Reaction

The oxidation step to convert one or more intermediates (e.g., HMF, DHMF, and/or FFA) into FDCA may be carried out using any suitable methods or techniques known in the art.

For example, in one embodiment, FFA undergoes oxidation to produce FDCA. In another embodiment, DEHU is oxidized to produce (2S)-DOHA. In yet another embodiment, DTHU is oxidized to produce (2R)-DOHA.

a) Oxidants

The oxidation reaction may be carried out using any suitable oxidants, including oxidation catalysts. In some embodiments, the oxidant may include bromine, nitric acid, peroxide (e.g., sodium peroxide), TEMPO and TEMPO-like nitroxide oxidation catalysts (e.g., 4-acetamido-TEMPO), platinum catalysts (e.g., platinum on carbon, platinum on silica, platinum on titanium dioxide, platinum on alumina), gold catalysts (e.g., gold sponge, gold on carbon, gold on titanium dioxide), palladium catalysts (e.g., palladium on carbon), rhodium catalysts (e.g., rhodium on carbon), copper catalysts, molybdenum catalysts, vanadium, titanium catalysts, cobalt catalysts, nickel catalysts, or iron catalysts.

The oxidant may be a solid catalyst. In some embodiments, the oxidant is a solid catalyst that may be heterogeneous with the solvent system used in the reaction. Suitable oxidants used in solid form may include, for example, platinum on a solid support (e.g., platinum on carbon, platinum on silica, platinum on titanium dioxide, platinum on alumina), gold on a solid support (e.g., gold sponge, gold on carbon, gold on titanium dioxide), palladium on a solid support (e.g., palladium on carbon), and rhodium on a solid support (e.g., rhodium on carbon).

b) Reaction Conditions

The reaction time and temperature of the oxidation reaction may vary depending on the starting materials and oxidants used.

In some embodiments, the reaction mixture containing the one or more intermediates (e.g., HMF, DHMF, and/or FFA) may be heated to a temperature sufficient to form FDCA. In other embodiments, the reaction mixture containing DEHU may be heated to a temperature sufficient to form DOHA. In yet other embodiments, the reaction mixture containing DTHU may be heated to a temperature sufficient to form DOHA.

In some embodiments, the reaction mixture may be heated to reflux. In other embodiments, the reaction mixture may be heated to between 40° C. and 100° C., between 45° C. and 80° C., between 45° C. and 60° C., or between 50° C. and 75° C. In some embodiments, the reaction mixture may be performed at room temperature.

In some embodiments, the reaction time may be less than 1 minute, between 5-10 minutes, about 1 hour, about 5 hours, about 24 hours, about 48 hours, between 1-72 hours, between 1-24 hours, between 1-10 hours, or between 1-5 hours.

c) Enzymatic Oxidation

In some embodiments, the oxidation step may be carried out by enzymatic oxidation. Suitable enzymes for oxidation may include, for example, aldehyde dehydrogenase.

Isolation of FDCA

One skilled in the art would recognize the various methods or techniques that may be employed to isolate FDCA from the reaction mixture. In some embodiments, the reaction mixture containing FDCA may be isolated by filtration. In other embodiments, FDCA may be isolated by solvent extraction. In some embodiments, the extraction process is a continuous extraction process. In yet other embodiments, FDCA may be isolated by distillation, column chromatography (e.g., using silica gel), or crystallization. A combination of isolation methods described herein may also be used.

Reaction Yield

Unless otherwise stated, "yield" as used herein refers to the theoretical maximum of a product that may be prepared from the amount of starting materials used. For example, in some embodiments where DEHU or DTHU is the starting material, the yield refers to the theoretical maximum of FDCA that may be produced from the amount of DEHU or DTHU used. In other embodiments, the yield refers to the theoretical maximum of FFA that may be produced from the amount of DEHU or DTHU used. In yet other embodiments where seaweed is the starting material, the yield refers to the theoretical maximum of FDCA that may be produced from the amount of seaweed used. In yet other embodiments where alginate is the starting material, the yield refers to the theoretical maximum of FDCA that may be produced from the amount of alginate used. In yet other embodiments where pectin is the starting material, the yield refers to the theoretical maximum of FDCA that may be produced from the amount of pectin used. In certain embodiments, the yield refers to the theoretical maximum of FFA that may be produced from the amount of starting materials used.

In some embodiments, the methods described herein yield at least 20%, at least 30%, at least 40%, at least 50%, at least 55%, at least 60%, at least 65%, at least 70%, at least 75%, at least 80%, at least 85%, at least 90%, at least 95%, or at least 99% of the theoretical maximum of FDCA that may be produced from the DEHU used as the starting material.

In some embodiments, the methods described herein yield at least 20%, at least 30%, at least 40%, at least 50%, at least 55%, at least 60%, at least 65%, at least 70%, at least 75%, at least 80%, at least 85%, at least 90%, at least 95%, or at least 99% of the theoretical maximum of FDCA that may be produced from the DTHU used as the starting material.

In other embodiments, the methods described herein yield between 20% and 100%, between 20% and 90%, between 20% and 80%, between 30% and 100%, between 30% and 90%, between 30% and 80%, between 40% and 100%, between 40% and 90%, between 40% and 80%, between 40% and 70%, between 40% and 60%, between 50% and 100%, between 50% and 90%, between 50% and 80%, between 50% and 70%, between 55% and 95%, between 55% and 90%, between 55% and 85%, between 55% and 80%, between 55% and 75%, between 55% and 70%, between 60% and 99%, between 60% and 95%, between 60% and 90%, between 60% and 80%, between 65% and 99%, between 65% and 90%, between 65% and 85%, between 65% and 80%, between 70% and 99%, between 70% and 95%, between 70% and 90%, between 70% and 85%, between 75% and 99%, between 75% and 95%, between 75% and 90%, between 75% and 85%, between 80% and 99%, between 85% and 99%, or between 90% and 99% the theoretical maximum of FDCA that may be produced from the DEHU used as the starting material.

In other embodiments, the methods described herein yield between 20% and 100%, between 20% and 90%, between 20% and 80%, between 30% and 100%, between 30% and 90%, between 30% and 80%, between 40% and 100%, between 40% and 90%, between 40% and 80%, between 40% and 70%, between 40% and 60%, between 50% and 100%, between 50% and 90%, between 50% and 80%, between 50% and 70%, between 55% and 95%, between 55% and 90%, between 55% and 85%, between 55% and 80%, between 55% and 75%, between 55% and 70%, between 60% and 99%, between 60% and 95%, between 60% and 90%, between 60% and 80%, between 65% and 99%, between 65% and 90%, between 65% and 85%, between 65% and 80%, between 70% and 99%, between 70% and 95%, between 70% and 90%, between 70% and 85%, between 75% and 99%, between 75% and 95%, between 75% and 90%, between 75% and 85%, between 80% and 99%, between 85% and 99%, or between 90% and 99% the theoretical maximum of FDCA that may be produced from the DTHU used as the starting material.

In yet other embodiments, the methods described herein yield at least 20%, at least 30%, at least 40%, at least 50%, at least 55%, at least 60%, at least 65%, at least 70%, at least 75%, at least 80%, at least 85%, at least 90%, at least 95%, or at least 99% of the theoretical maximum of FDCA that may be produced from the seaweed, alginate, oligoalginate, alginate monomers (e.g., mannuronate and guluronate) pectin, oligopectin, polygalacturonate, galacturonate, and/or oligogalacturonate used as the starting material.

In yet other embodiments, the methods described herein yield between 20% and 100%, between 20% and 90%, between 20% and 80%, between 30% and 100%, between 30% and 90%, between 30% and 80%, between 40% and 100%, between 40% and 90%, between 40% and 80%, between 40% and 70%, between 40% and 60%, between 50% and 100%, between 50% and 90%, between 50% and 80%, between 50% and 70%, between 55% and 95%, between 55% and 90%, between 55% and 85%, between 55% and 80%, between 55% and 75%, between 55% and 70%, between 60% and 99%, between 60% and 95%, between 60% and 90%, between 60% and 80%, between 65% and 99%, between 65% and 90%, between 65% and 85%, between 65% and 80%, between 70% and 99%, between 70% and 95%, between 70% and 90%, between 70% and 85%, between 75% and 99%, between 75% and 95%, between 75% and 90%, between 75% and 85%, between 80% and 99%, between 85% and 99%, or between 90% and 99% the theoretical maximum of FDCA that may be produced from the seaweed, alginate, oligoalginate, alginate monomers (e.g., mannuronate and guluronate), pectin, oligopectin, polygalacturonate, galacturonate, and/or oligogalacturonate used as the starting material.

of the reactions described in this example are summarized in Table 1 below. For the reactions with the lower starting material concentration, 0.125 mL of water was added to the reaction mixture.

TABLE 1

Summary of the concentration starting materials, and products (FFA and 2-furancarboxylic acid)

| Acid treatment | Starting material (relative concentration level) | Starting material concentration (mM) | FFA (mM) | 2-furancarboxylic acid (mM) |
| --- | --- | --- | --- | --- |
| 0.2M $H_2SO_4$ | glucose (low) | 1.44 | 0 | 0 |
| 0.2M $H_2SO_4$ | glucose (high) | 5.39 | 0 | 0 |
| 0.2M $H_2SO_4$ | DEHU (low) | 0.38 | 0 | 0 |
| 0.2M $H_2SO_4$ | DEHU (high) | 1.81 | 0.007 | 0.0572 |
| 16M $H_2SO_4$ | glucose (low) | 1.07 | 0 | 0 |
| 16M $H_2SO_4$ | glucose (high) | 3.34 | 0.000 | 0 |
| 16M $H_2SO_4$ | DEHU (low) | 0.34 | 0.039 | 0.0212 |
| 16M $H_2SO_4$ | DEHU (high) | 1.61 | 0.087 | 0.114 |
| 10.7M $H_2SO$ | glucose (low) | 1.01 | 0 | 0 |
| 10.7M $H_2SO$ | glucose (high) | 3.81 | 0 | 0 |
| 10.7M $H_2SO$ | DEHU (low) | 0.34 | 0.004 | 0.0301 |
| 10.7M $H_2SO$ | DEHU (high) | 1.61 | 0.071 | 0.1746 |

EXAMPLES

The following examples are merely illustrative and are not meant to limit any aspects of the present disclosure in any way.

Unless otherwise specified, starting materials and reagents may be obtained from well-known commercial supply houses, e.g., Aldrich Chemical Company (Milwaukee, Wis.), and are of standard grade and purity; or may be obtained by procedures described in the art or adapted therefrom, where suitable procedures may be identified through the Chemical Abstracts and Indices therefor, as developed and published by the American Chemical Society.

Example 1

Conversion of DEHU into FFA

This example demonstrates the acid-catalyzed dehydration and cyclization of DEHU to yield FFA based on three different sulfuric acid treatments (0.2M, 10.7M, and 16 M sulfuric acid).
Materials and Methods
DEHU was first obtained by enzymatic degradation of alginate. Sodium alginate was combined with sterilized water. Sigma alginate lyase and oligoalginate lyase cleared lysate (from LB culture pellet) was then added to the sodium alginate solution. This reaction proceeded for about 18-24 hours, and DEHU was isolated. The DEHU obtained from this enzymatic degradation of alginate was used in the following reactions.

The starting materials in this example include glucose and DEHU. The concentrations of starting materials used in each In the first acid treatment, each starting material was combined with 0.2M sulfuric acid (10 mL).

In the second acid treatment, each starting material was combined with 2% sodium chloride (0.125 mL) and 98% sulfuric acid (2 mL). The final sulfuric acid concentration was 16 M.

In the third acid treatment, each starting material was combined with 2% sodium chloride (0.125 mL) and 72% sulfuric acid (2 mL). The final sulfuric acid concentration was 10.7 M.

Each reaction mixture was heated to 70° C. After 3.1 hours, a sample from each reaction mixture was obtained and analyzed by HPLC to determine the production of FFA. All reaction samples were analyzed by retention time studies on a Shimadzu High Performance Liquid Chromatography system. The method for detection was performed on a Phenomenex-Rezex ROA, using an organic acid H+ column 300×7.80 mm, with 5 mM sulfuric acid mobile phase with a flow rate of 0.5 mL/min.
Analysis Table 1 above summarizes the product yields for FFA and 2-furancarboxylic acid observed in each reaction mixture. The data from this table was used to generate FIGS. 6 and 7.

Figure 6:
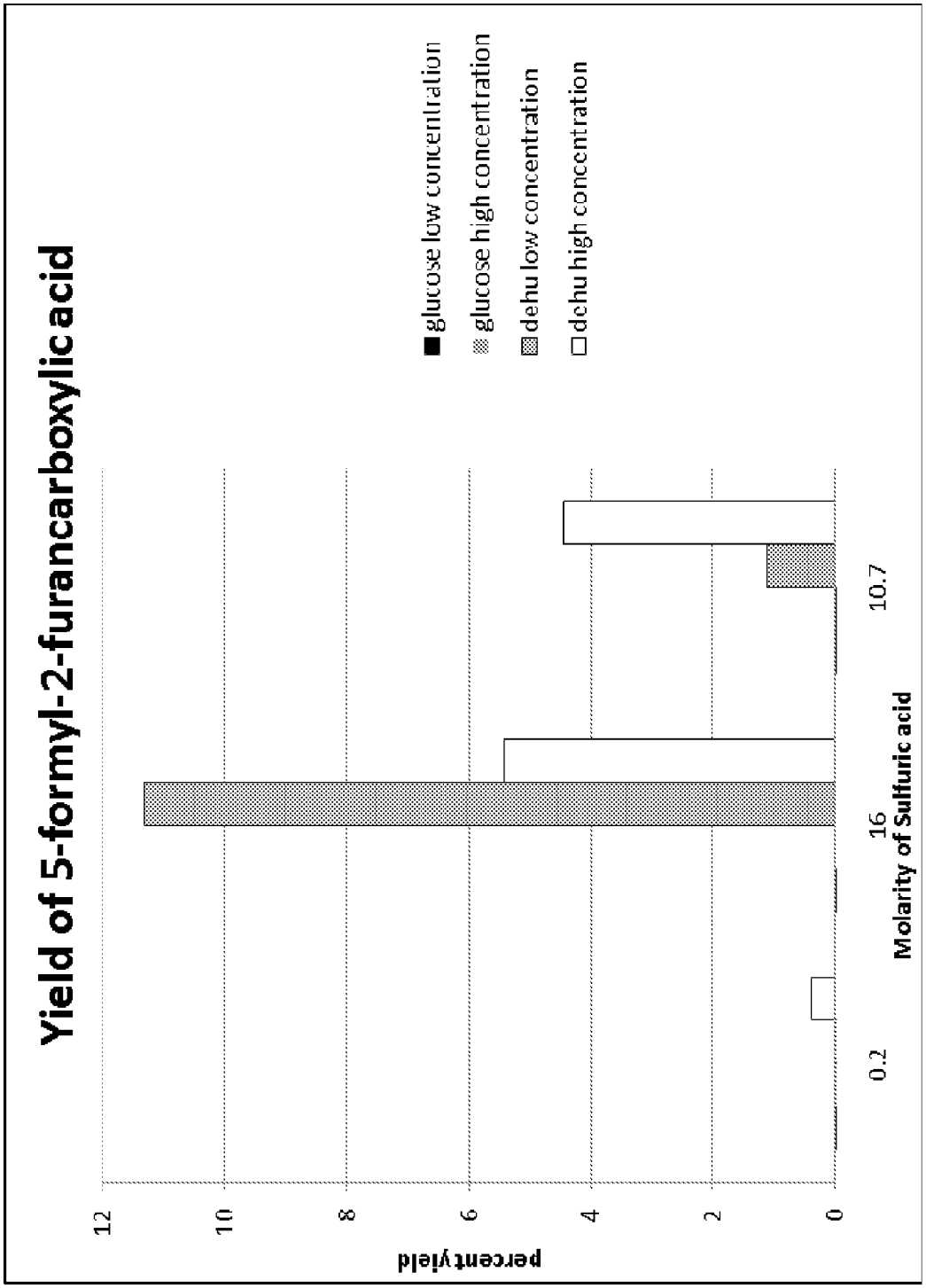
FIG. 6 is a graph depicting the yield of FFA produced from (a) DEHU and (b) glucose using sulfuric acid treatments of 0.2 M, 16 M, and 10.7 M concentrations.

As seen in FIG. 6, FFA was observed in the reactions using 16M and 10.7 M sulfuric acid treatments. The stronger acid treatment was observed to produce a higher FFA yield.

Figure 7:
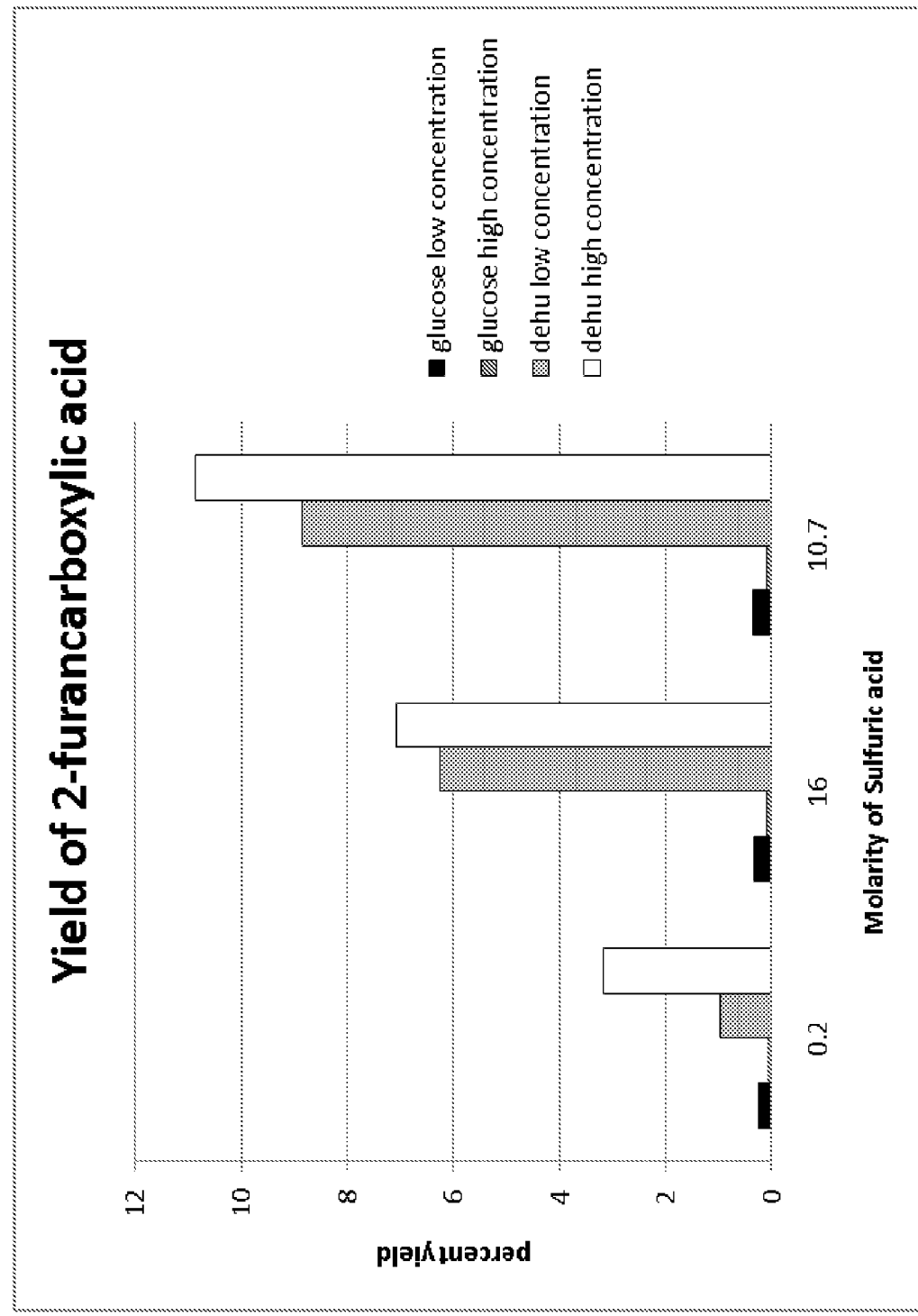
FIG. 7 is a graph depicting the yield of 2-furancarboxylic acid produced from (a) DEHU and (b) glucose using sulfuric acid treatments of 0.2 M, 16 M, and 10.7 M concentrations.

As seen in FIG. 7, 2-furancarboxylic acid was also observed in the reaction mixture. The treatment using 10.7 M sulfuric acid was observed to provide a higher yield of 2-furancarboxylic acid.

Example 2

Conversion of DOHA and DEHU into FFA

This example demonstrates the acid-catalyzed dehydration and cyclization of DOHA and DEHU to yield FDCA and FFA in the presence of sulfuric acid and sodium tetraborate decahydrate, respectively.
Materials and Methods
The starting materials in this example include DOHA, galacturonate, and DEHU. The DEHU was first obtained by enzymatic degradation of alginate according to the procedure described in Example 1 above. The DOHA was obtained by oxidizing a solution of the DEHU obtained by enzymatic degradation of alginate according to the procedure described in Example 1 above.

The concentrations of starting materials used in each of the reactions described in this example are summarized in Table 2 below. For the reactions with the lower starting material concentration, 500 uL of water was added to the reaction mixture.

TABLE 2

Summary of the concentration starting materials, and products (FFA and 2-furancarboxylic acid)

| Starting material (relative concentration level) | Starting material concentration (mM) | FFA (mM) | 2-furancarboxylic acid (mM) |
|---|---|---|---|
| DOHA (low) | 0.29 | 0.084 | 0.040 |
| DOHA (high) | 1.43 | 0.172 | 0.134 |
| galacturonate (low) | 0.77 | 0.106 | 0 |
| galacturonate (high) | 2.83 | 0.430 | 0 |
| DEHU (low) | 0.26 | 0.058 | 0.036 |
| DEHU (high) | 1.32 | 0.113 | 0.146 |

Each starting material was combined with 98% sulfuric acid (2 mL) and sodium tetraborate decahydrate (75 mM). Each reaction mixture was heated to 70° C. After 10 minutes, a sample from each reaction mixture was obtained and analyzed by HPLC according to the procedure described in Example 1 above to determine the production of FFA.

Analysis

Table 2 above summarizes the product yields for FFA and 2-furancarboxylic acid observed in each reaction mixture. The data from this table was used to generate FIGS. 8 and 9.

Figure 8:
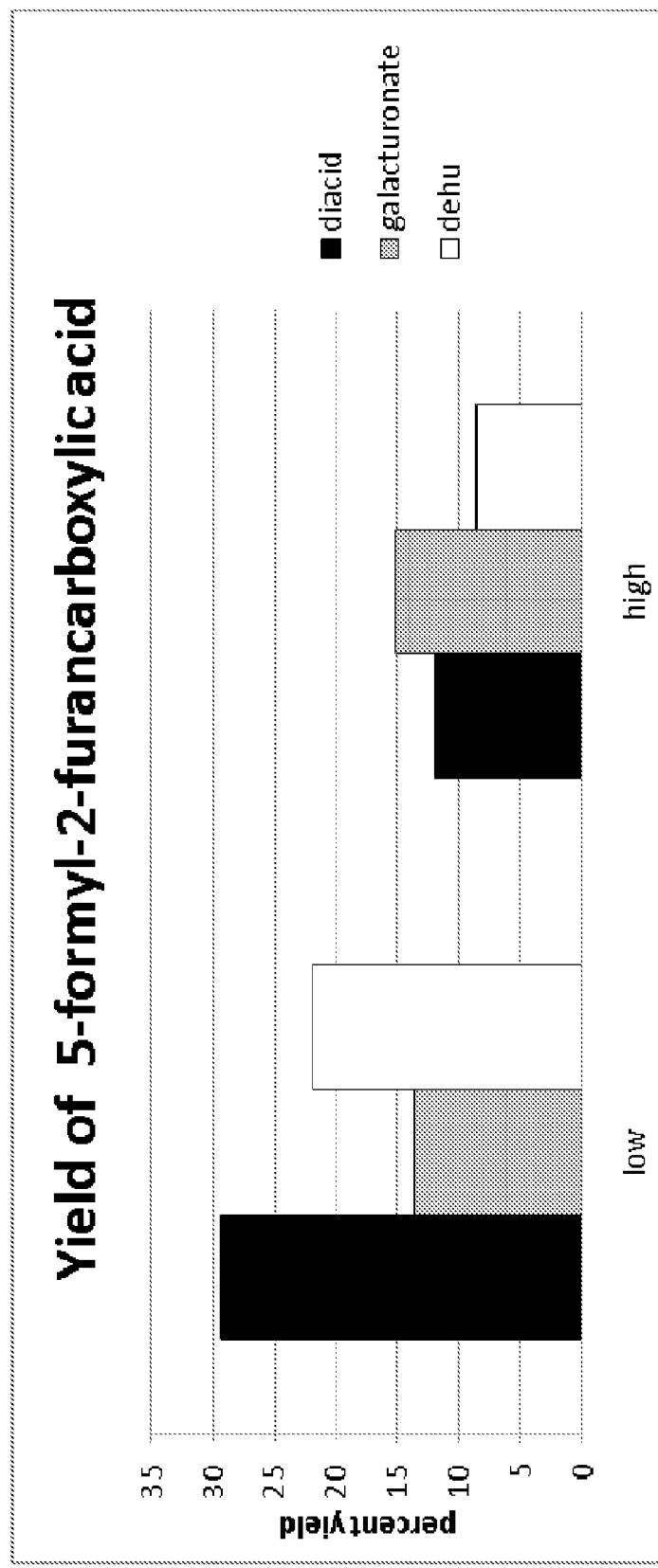
FIG. 8 is a graph depicting the yield of FFA produced from (a) 2,3-dihydroxy-5-oxohexanedioic acid ("DOHA"), (b) galacturonate, and (c) DEHU in the presence of sulfuric acid and sodium tetraborate decahydrate.

As seen FIG. 8, FFA was observed in all the reactions. The reactions with a lower starting material concentration were generally observed to produce a higher FFA yield than the reactions with a higher starting material concentration (e.g., for DOHA and DEHU). In this Example, FFA was formed from a DOHA. It should be understood, however, that DOHA can be directly transformed into FDCA. FFA formation is due to the remaining DEHU in the solution.

Figure 9:
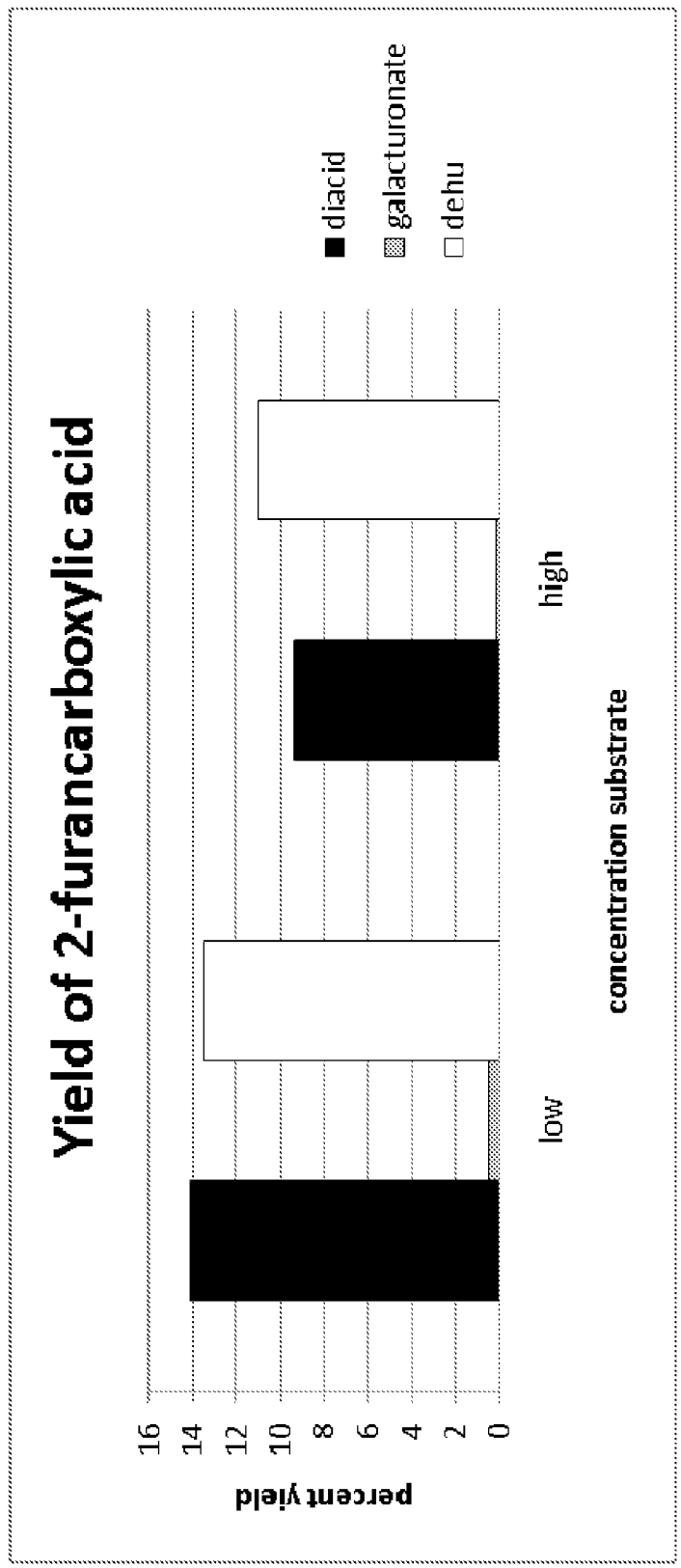
FIG. 9 is a graph depicting the yield of 2-furancarboxylic acid produced from (a) DOHA, (b) galacturonate, and (c) DEHU in the presence of sulfuric acid and sodium tetraborate decahydrate.

As seen in FIG. 9, when DOHA and DEHU were used as starting materials, 2-furancarboxylic acid was also observed in the reaction mixture.

Example 3

Conversion of DEHU and DOHA into FFA and FDCA

This example demonstrates the acid-catalyzed dehydration and cyclization of DEHU and DOHA to yield FFA and FDCA in the presence of five different sulfuric acid treatments and sodium tetraborate decahydrate, respectively.

Materials and Methods

The starting materials in this example include galacturonate, DEHU, and DOHA. DEHU and DOHA were obtained according to the procedure described in Examples 1 and 2 above.

The concentrations of starting materials used in each of the reactions described in this example are summarized in Table 3 below.

TABLE 3

Summary of the concentration starting materials, and products (FFA and 2-furancarboxylic acid)

| Acid treatment | Starting material | Starting material concentration (mM) | FFA (mM) | 2-furancarboxylic acid (mM) |
|---|---|---|---|---|
| 16M $H_2SO_4$ | galacturonate | 0.32 | 0.119 | 0 |
| 16M $H_2SO_4$ | DEHU | 0.37 | 0.066 | 0.066 |
| 16M $H_2SO_4$ | DOHA | 0.38 | 0.116 | 0.051 |
| 14.4M $H_2SO_4$ | galacturonate | 0.31 | 0.054 | 0 |
| 14.4M $H_2SO_4$ | DEHU | 0.37 | 0.044 | 0.061 |
| 14.4M $H_2SO_4$ | DOHA | 0.37 | 0.051 | 0.043 |
| 10.7M $H_2SO_4$ | galacturonate | 0.32 | 0.002 | 0 |
| 10.7M $H_2SO_4$ | DEHU | 0.37 | 0.036 | 0.089 |
| 10.7M $H_2SO_4$ | DOHA | 0.38 | 0.043 | 0.075 |
| 8M $H_2SO_4$ | galacturonate | 0.30 | 0 | 0 |
| 8M $H_2SO_4$ | DEHU | 0.36 | 0.035 | 0.076 |
| 8M $H_2SO_4$ | DOHA | 0.36 | 0.034 | 0.072 |
| 5M $H_2SO_4$ | galacturonate | 0.31 | 0 | 0 |
| 5M $H_2SO_4$ | DEHU | 0.37 | 0.005 | 0.020 |
| 5M $H_2SO_4$ | DOHA | 0.37 | 0.013 | 0.037 |

In the first acid treatment, each of starting materials was combined with water (0.125 mL), 98% sulfuric acid (2 mL), and sodium tetraborate decahydrate (75 mM). The final sulfuric acid concentration was 16 M.

In the second acid treatment, each starting material was combined with water (0.375 mL), 98% sulfuric acid (2 mL), and sodium tetraborate decahydrate (75 mM). The final sulfuric acid concentration was 14.4 M.

In the third acid treatment, each starting material was combined with water (0.125 mL), 72% sulfuric acid (2 mL), and sodium tetraborate decahydrate (75 mM). The final sulfuric acid concentration was 10.7 M.

In the fourth acid treatment, each starting material was combined with water (0.875 mL), 72% sulfuric acid (2 mL), and sodium tetraborate decahydrate (75 mM). The final sulfuric acid concentration was 8 M.

In one reaction of the fifth acid treatment, each starting material was combined with water (1.275 mL), 72% sulfuric acid (1 mL), and sodium tetraborate decahydrate (75 mM). The final sulfuric acid concentration was 5 M.

Each reaction mixture was heated to 70° C. After 10 minutes, a sample from each reaction mixture was obtained and analyzed by HPLC according to the procedure described in Example 1 above to determine the production of FFA.

Analysis

Table 3 above summarizes the product yields for FFA and 2-furancarboxylic acid observed in each reaction mixture. The data from this table was used to generate FIGS. 10 and 11.

Figure 10:
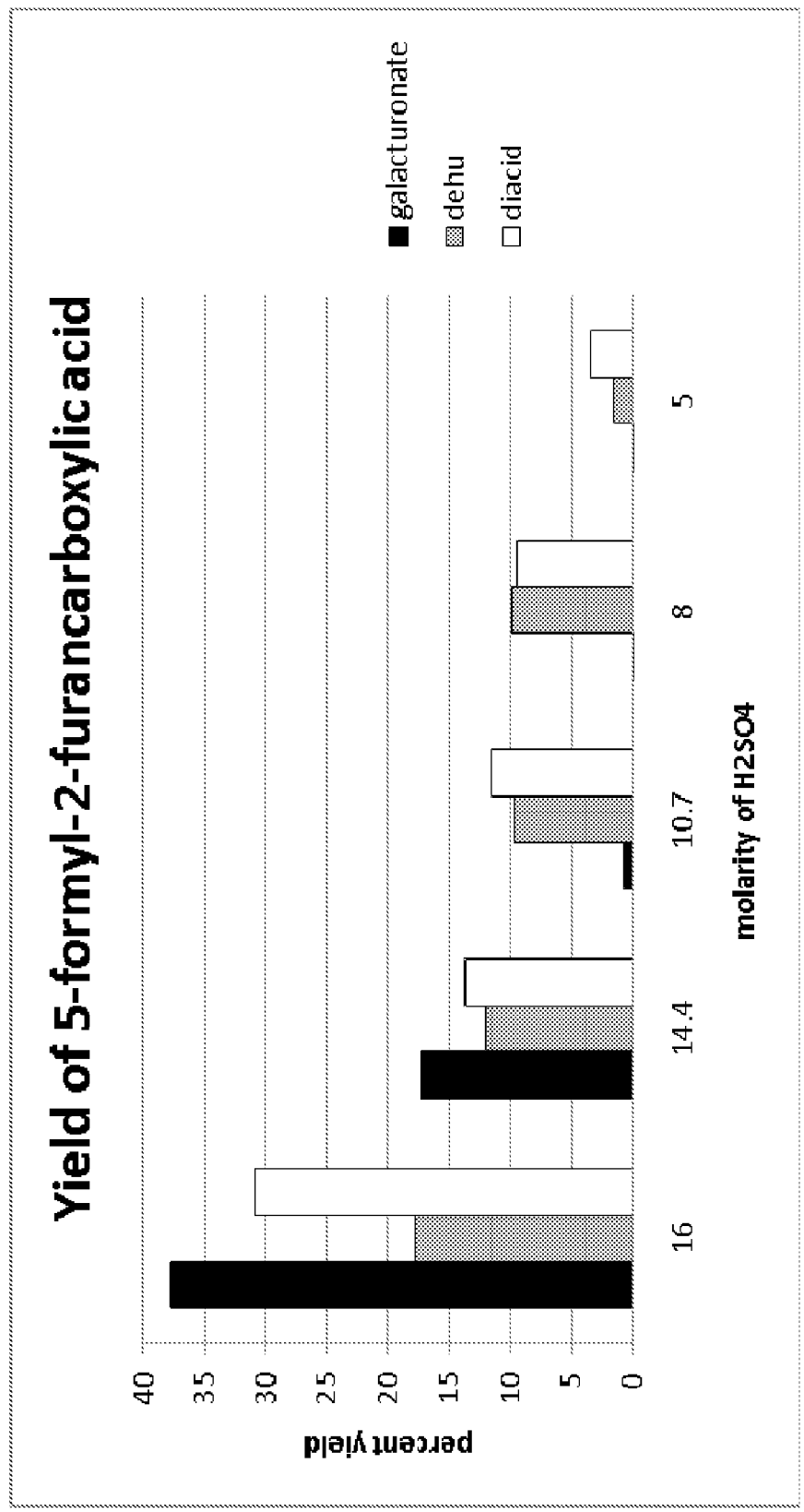
FIG. 10 is a graph depicting the yield of FFA produced from (a) galacturonate, (b) DEHU and (c) DOHA using sulfuric acid treatments of 16 M, 14.4 M, 10.7 M, 8M, and 5M concentrations.

As seen in FIG. 10, DEHU and DOHA were observed to produce FFA using all the acid treatments; however, the stronger acid treatments were observed to produce higher FFA yields. Galacturonate was observed to produce FFA when stronger acid treatments were used (e.g., 16 M, 14.4 M). In this Example, FFA was formed from a DOHA-containing substrate. It should be understood, however, that DOHA can be directly transformed into FDCA. The FFA formation from DOHA is due to the remaining DEHU in this solution.

Figure 11:
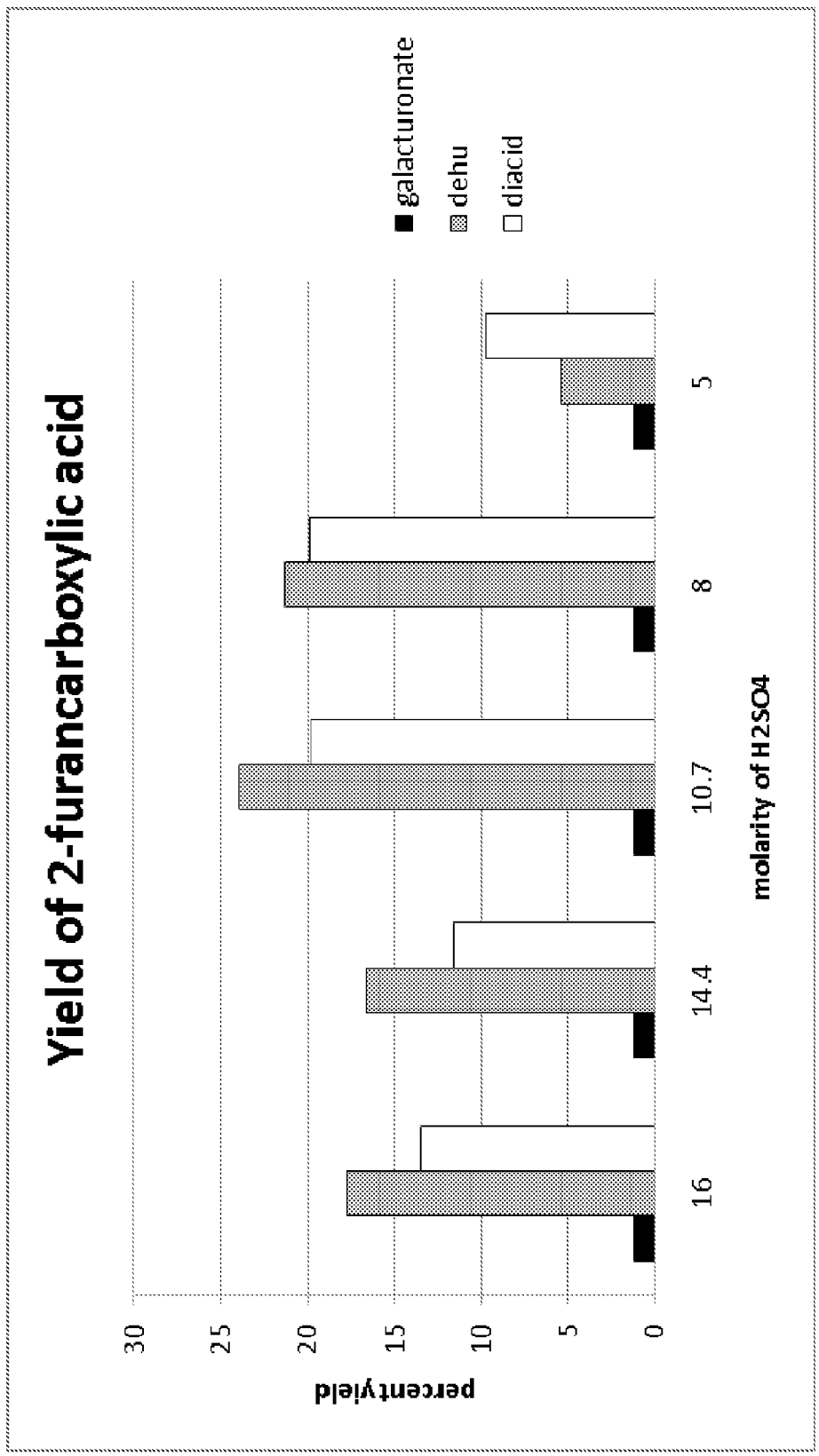
FIG. 11 is a graph depicting the yield of 2-furancarboxylic acid produced from (a) galacturonate, (b) DEHU and (c) DOHA using sulfuric acid treatments of 16 M, 14.4 M, 10.7 M, 8M, and 5M concentrations.

As seen in FIG. 11, DEHU and DOHA were observed to produce 2-furancarboxylic acid in the reaction mixture. It was also observed that for the DEHU and DOHA reactions, a 10.7 M sulfuric acid treatment yielded a higher percentage of 2-furancarboxylic acid compared to the other acid treatments.

Example 4

Conversion of FFA into FDCA

This example demonstrates oxidation of FFA to produce FDCA.

Materials and Methods

FFA was obtained from Technical Chemical Laboratories, and used without further purification. FDCA was purchased from Technical Chemical Laboratories, and used as an analytical standard. Sodium hydroxide (NaOH) pellets and 5% platinum on carbon were purchased from Sigma Aldrich. Compressed nitrogen was purchased from AIRGAS. Air was supplied from a compressor.

In a Sartorius bioreactor, 0.3 g of FFA was dissolved in 600 mL of 1M NaOH. The solution was purged with nitrogen gas for about 15 minutes (1 L/min flow rate, 250 rpm), while the reaction temperature was increased to 55° C. After the temperature reached 55° C., 0.3 grams of 5% platinum on carbon was introduced into the reactor. At this time, a sample was taken. The platinum catalyst was filtered from the sample, and the filtrate was stored at −20° C. The nitrogen gas was shut off. The air compressor was turned on and the flow rate was set to 1 L/min. Samples were taken at 0.5 hours, 17 hours, 24 hours and 60 hours.

The samples were analyzed using a Phenomenex ROA organic acid column and a mobile phase of 5 mM $H_2SO_4$ at a flow rate of 0.6 mL/min. The UV detector was set to 210 nm. Dilute standards of FFA and FDCA were injected using this method. The FFA standard eluted at a retention time of 20.5 minutes, and the FDCA standard at 15.5 minutes. A small peak corresponding to FDCA was observed in the FFA standard.

Analysis

Figure 12:
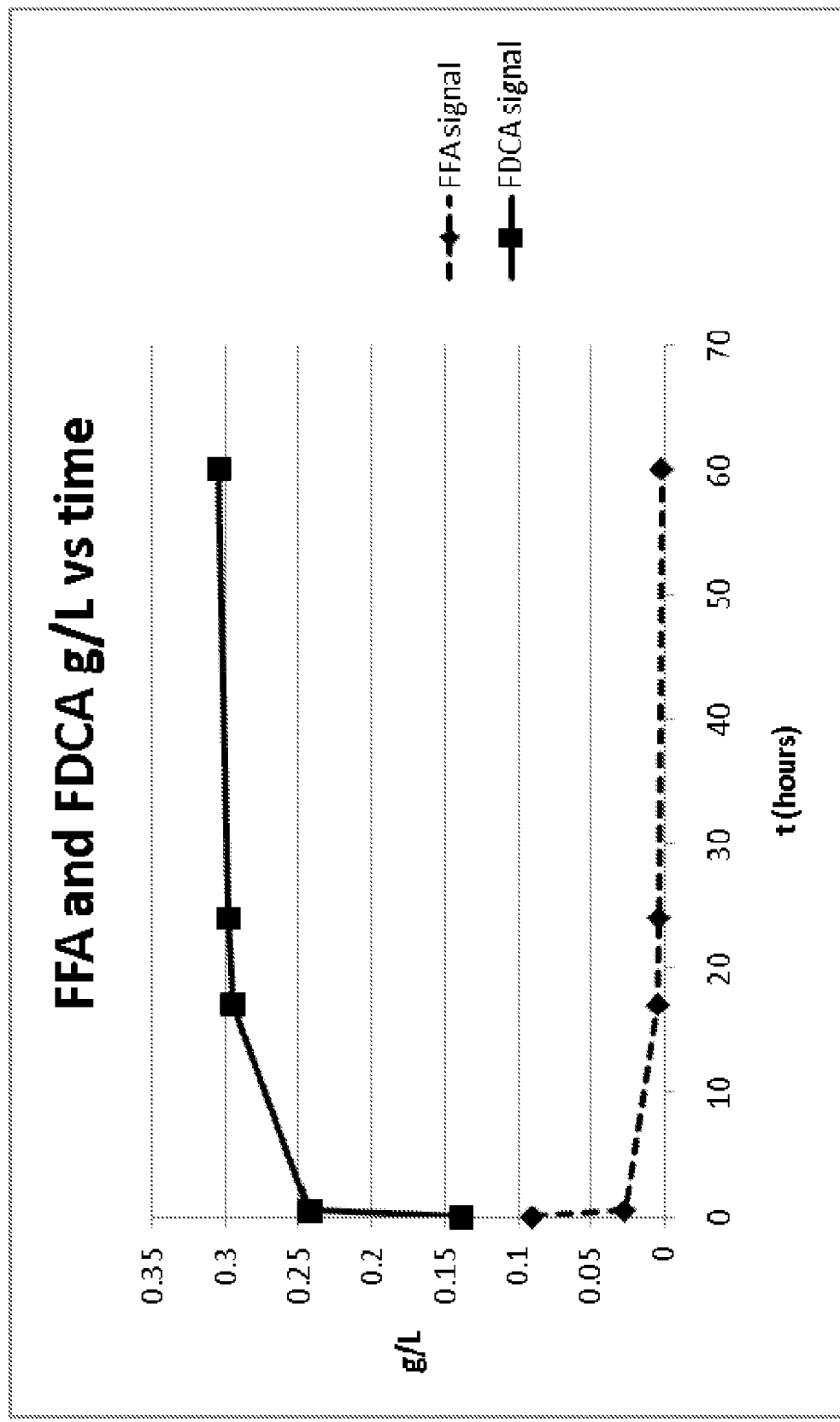
FIG. 12 is a graph depicting the production of FDCA and consumption of FFA over 60 hours.

As seen in FIG. 12, the oxidation reaction was observed to have proceeded quickly in the first few seconds after the platinum catalyst was introduced into the reactor.

Example 5

Conversion of DTHU into FFA

This example demonstrates the acid-catalyzed dehydration and cyclization of DTHU to yield FFA based on three different sulfuric acid treatments (0.2M, 10.7M, and 16 M sulfuric acid).

Materials and Methods

DTHU is first obtained by enzymatic degradation of pectin. The DTHU obtained from this enzymatic degradation of pectin is used in the following reactions.

The concentrations of starting materials that are used in each of the reactions described in this example are summarized in Table 4 below. For the reactions with the lower starting material concentration, 0.125 mL of water is added to the reaction mixture.

TABLE 4

Summary of the concentration starting materials

| Acid treatment | Starting material (relative concentration level) | Starting material concentration (mM) |
|---|---|---|
| 0.2M $H_2SO_4$ | DTHU (low) | 0.38 |
| 0.2M $H_2SO_4$ | DTHU (high) | 1.81 |
| 16M $H_2SO_4$ | DTHU (low) | 0.34 |
| 16M $H_2SO_4$ | DTHU (high) | 1.61 |
| 10.7M $H_2SO_4$ | DTHU (low) | 0.34 |
| 10.7M $H_2SO_4$ | DTHU (high) | 1.61 |

In the first acid treatment, the starting material is combined with 0.2M sulfuric acid (10 mL).

In the second acid treatment, the starting material is combined with 2% sodium chloride (0.125 mL) and 98% sulfuric acid (2 mL). The final sulfuric acid concentration is 16 M.

In the third acid treatment, the starting material is combined with 2% sodium chloride (0.125 mL) and 72% sulfuric acid (2 mL). The final sulfuric acid concentration is 10.7 M.

Each reaction mixture is heated to 70° C. After 3.1 hours, a sample from each reaction mixture is obtained and analyzed by HPLC according the procedure described in Example 1 above.

Example 6

Conversion of DTHU into FFA

This example demonstrates the acid-catalyzed dehydration and cyclization of DTHU to yield FFA in the presence of sulfuric acid and sodium tetraborate decahydrate.

Materials and Methods

DTHU is obtained by enzymatic degradation of pectin according to the procedure described in Example 5 above.

The concentrations of starting materials that are used in each of the reactions described in this example are summarized in Table 5 below. For the reactions with the lower starting material concentration, 500 uL of water is added to the reaction mixture.

TABLE 5

Summary of the concentration starting materials

| Starting material (relative concentration level) | Starting material concentration (mM) |
|---|---|
| DTHU (low) | 0.26 |
| DTHU (high) | 1.32 |

Each starting material is combined with 98% sulfuric acid (2 mL) and sodium tetraborate decahydrate (75 mM). Each reaction mixture is heated to 70° C. After 10 minutes, a sample from each reaction mixture is obtained and analyzed by HPLC according to the procedure described in Example 1 above to determine the production of FFA.

Example 7

Conversion of DTHU into FFA

This example demonstrates the acid-catalyzed dehydration and cyclization of DTHU to yield FFA in the presence of five different sulfuric acid treatments and sodium tetraborate decahydrate.

Materials and Methods

DTHU is obtained by enzymatic degradation of pectin according to the procedure described in Example 5 above.

The concentrations of starting materials used in each of the reactions described in this example are summarized in Table 6 below.

TABLE 6

Summary of the concentration starting materials

| Acid treatment | Starting material | Starting material concentration (mM) |
|---|---|---|
| 16M $H_2SO_4$ | DTHU | 0.37 |
| 14.4M $H_2SO_4$ | DTHU | 0.37 |
| 10.7M $H_2SO_4$ | DTHU | 0.37 |
| 8M $H_2SO_4$ | DTHU | 0.36 |
| 5M $H_2SO_4$ | DTHU | 0.37 |

In the first acid treatment, the starting material is combined with water (0.125 mL), 98% sulfuric acid (2 mL), and sodium tetraborate decahydrate (75 mM). The final sulfuric acid concentration is 16 M.

In the second acid treatment, the starting material is combined with water (0.375 mL), 98% sulfuric acid (2 mL), and sodium tetraborate decahydrate (75 mM). The final sulfuric acid concentration is 14.4 M.

In the third acid treatment, the starting material is combined with water (0.125 mL), 72% sulfuric acid (2 mL), and sodium tetraborate decahydrate (75 mM). The final sulfuric acid concentration is 10.7 M.

In the fourth acid treatment, the starting material is combined with water (0.875 mL), 72% sulfuric acid (2 mL), and sodium tetraborate decahydrate (75 mM). The final sulfuric acid concentration is 8 M.

In one reaction of the fifth acid treatment, the starting material is combined with water (1.275 mL), 72% sulfuric acid (1 mL), and sodium tetraborate decahydrate (75 mM). The final sulfuric acid concentration is 5 M.

Each reaction mixture is heated to 70° C. After 10 minutes, a sample from each reaction mixture is obtained and analyzed by HPLC according to the procedure described in Example 1 above to determine the production of FFA.

Example 8

Conversion of Glucose, Pectin, Galacturonate and Alginate into FFA

This example demonstrates the acid-catalyzed dehydration and cyclization of glucose, pectin, galacturonate and alginate to yield FFA based on three different sulfuric acid treatments (0.2M, 10.7M, and 16M sulfuric acid).

Materials and Methods

The starting materials in this example include glucose, pectin, galacturonate, and alginate. The concentrations of starting materials used in each of the reactions described in this example are summarized in Table 7 below. For the reactions with the lower starting material concentration, 0.125 mL of water was added to the reaction mixture.

TABLE 7

Summary of the concentration starting materials, and products (FFA and 2-furancarboxylic acid)

| Acid treatment | Starting material (relative concentration level) | Starting material concentration (mM) | FFA (mM) | 2-furancarboxylic acid (mM) |
|---|---|---|---|---|
| 0.2M $H_2SO_4$ | glucose (low) | 1.44 | 0 | 0 |
| 0.2M $H_2SO_4$ | glucose (high) | 5.39 | 0 | 0 |
| 0.2M $H_2SO_4$ | pectin (low) | 0.73 | 0 | 0 |
| 0.2M $H_2SO_4$ | pectin (high) | 3.58 | 0 | 0 |
| 0.2M $H_2SO_4$ | galacturonate (low) | 1.16 | 0 | 0 |
| 0.2M $H_2SO_4$ | galacturonate (high) | 2.77 | 0 | 0 |

TABLE 7-continued

Summary of the concentration starting materials, and products (FFA and 2-furancarboxylic acid)

| Acid treatment | Starting material (relative concentration level) | Starting material concentration (mM) | FFA (mM) | 2-furancarboxylic acid (mM) |
|---|---|---|---|---|
| 0.2M $H_2SO_4$ | alginate (low) | 3.68 | 0 | 0 |
| 0.2M $H_2SO_4$ | alginate (high) | 0.89 | 0 | 0 |
| 16M $H_2SO_4$ | glucose (low) | 1.07 | 0 | 0 |
| 16M $H_2SO_4$ | glucose (high) | 3.34 | 0.000 | 0 |
| 16M $H_2SO_4$ | pectin (low) | 0.75 | 0.189 | 0 |
| 16M $H_2SO_4$ | pectin (high) | 3.21 | 0.614 | 0 |
| 16M $H_2SO_4$ | galacturonate (low) | 1.18 | 0.574 | 0 |
| 16M $H_2SO_4$ | galacturonate (high) | 3.23 | 1.220 | 0 |
| 16M $H_2SO_4$ | alginate (low) | 1.68 | 0.046 | 0 |
| 16M $H_2SO_4$ | alginate (high) | 3.36 | 0.040 | 0 |
| 10.7M $H_2SO_4$ | glucose (low) | 1.01 | 0 | 0 |
| 10.7M $H_2SO_4$ | glucose (high) | 1.44 | 0 | 0 |
| 10.7M $H_2SO_4$ | pectin (low) | 5.39 | 0 | 0 |
| 10.7M $H_2SO_4$ | pectin (high) | 0.73 | 0 | 0 |
| 10.7M $H_2SO_4$ | galacturonate (low) | 3.58 | 0 | 0 |
| 10.7M $H_2SO_4$ | galacturonate (high) | 1.16 | 0 | 0 |
| 10.7M $H_2SO_4$ | alginate (low) | 2.77 | 0 | 0 |
| 10.7M $H_2SO_4$ | alginate (high) | 3.68 | 0 | 0 |

In the first acid treatment, each starting material was combined with 0.2M sulfuric acid (10 mL).

In the second acid treatment, each starting material was combined with 2% sodium chloride (0.125 mL) and 98% sulfuric acid (2 mL). The final sulfuric acid concentration was 16 M.

In the third acid treatment, each starting material was combined with 2% sodium chloride (0.125 mL) and 72% sulfuric acid (2 mL). The final sulfuric acid concentration was 10.7 M.

Each reaction mixture was heated to 70° C. After 3.1 hours, a sample from each reaction mixture was obtained and analyzed by HPLC to determine the production of FFA. All reaction samples were analyzed by retention time studies on a Shimadzu High Performance Liquid Chromatography system. The method for detection was performed on a Phenomenex-Rezex ROA, using an organic acid H+ column 300×7.80 mm, with 5 mM sulfuric acid mobile phase with a flow rate of 0.5 mL/min.

Analysis

Table 7 above summarizes the product yields for FFA and 2-furancarboxylic acid observed in each reaction mixture. The data from this table was used to generate FIGS. 15 and 16.

Figure 15:
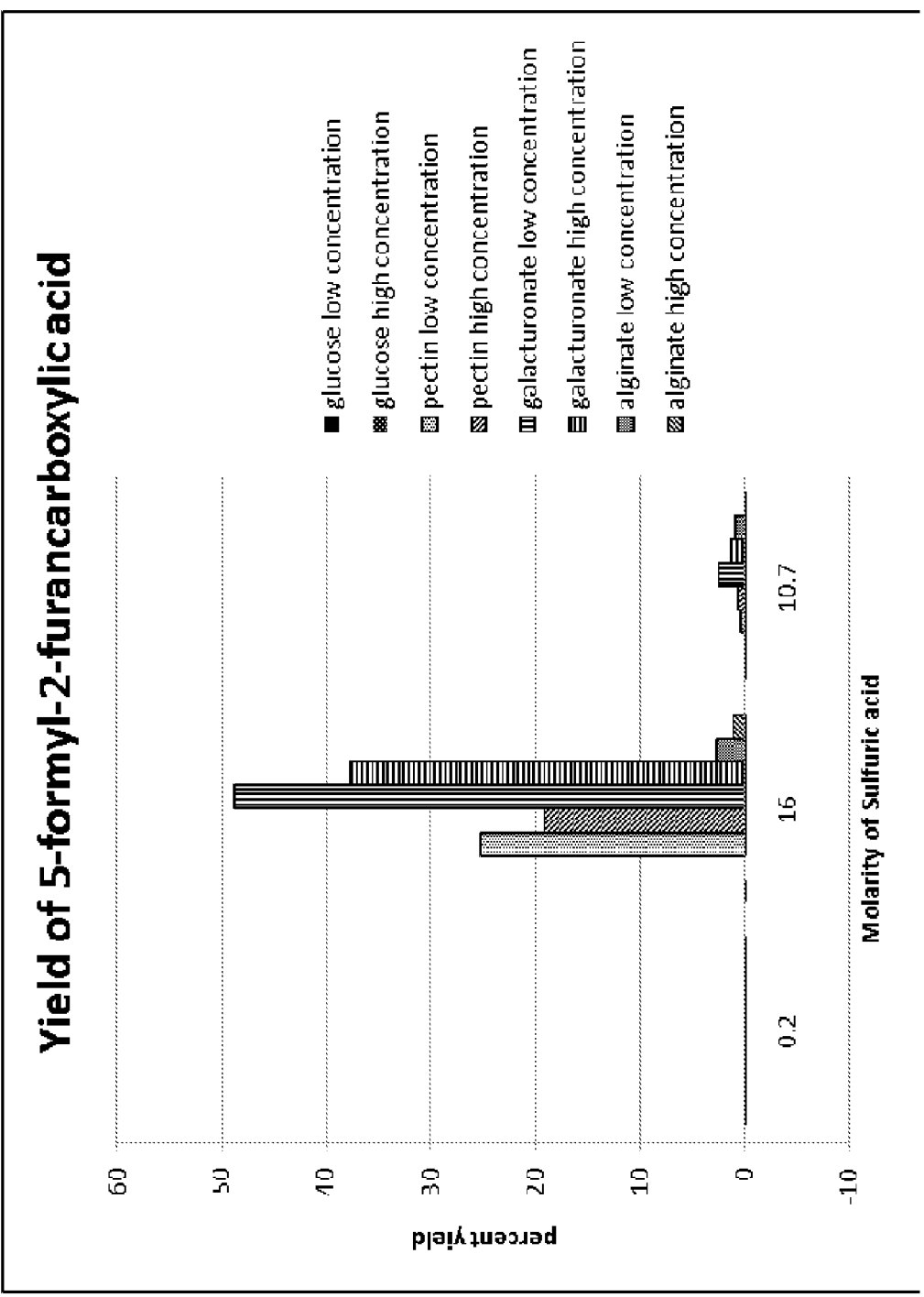
FIG. 15 is a graph depicting the yield of FFA produced from (a) glucose, (b) pectin, (c) galacturonate, and (d) alginate using sulfuric acid treatments of 0.2 M, 16 M, and 10.7 M concentrations.

As seen in FIG. 15, FFA was observed in the reactions using 16M sulfuric acid treatments. Thus, the stronger acid treatment was observed to produce a higher FFA yield.

Figure 16:
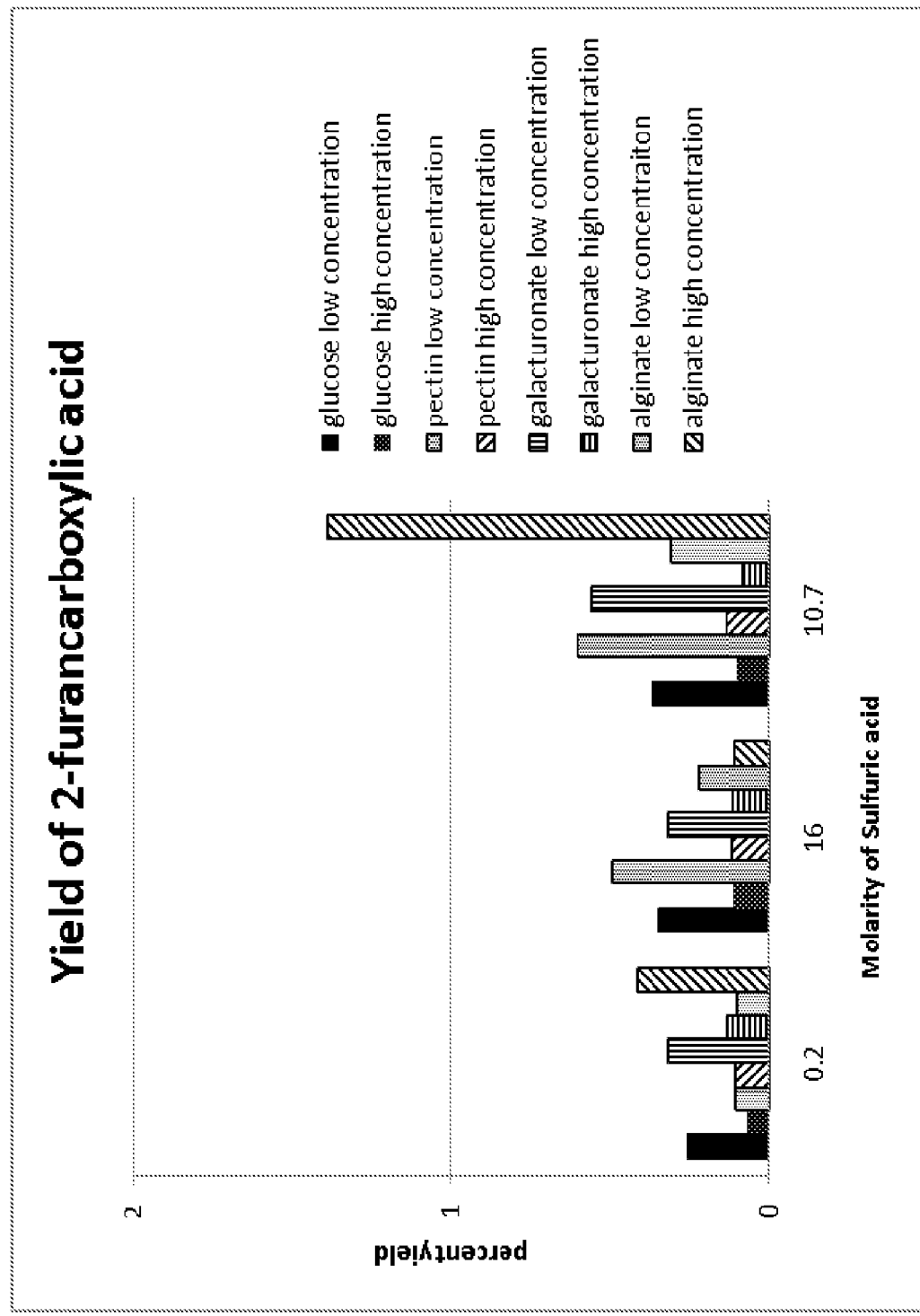
FIG. 16 is a graph depicting the yield of 2-furancarboxylic acid produced from (a) glucose, (b) pectin, (c) galacturonate, and (d) alginate using sulfuric acid treatments of 0.2 M, 16 M, and 10.7 M concentrations.

As seen in FIG. 16, trace amounts of 2-furancarboxylic acid were observed in the reaction mixtures.

Example 9

Conversion of Galacturonate and Alginate into FFA

This example demonstrates the acid-catalyzed dehydration and cyclization galacturonate and alginate to yield FFA in the presence of sulfuric acid and sodium tetraborate decahydrate.

Materials and Methods

The starting materials in this example include galacturonate and alginate. The concentrations of starting materials used in each of the reactions described in this example are summarized in Table 8 below. For the reactions with the lower starting material concentration, 500 uL of water was added to the reaction mixture.

TABLE 8

Summary of the concentration starting materials, and products (FFA and 2-furancarboxylic acid)

| Starting material (relative concentration level) | Starting material concentration (mM) | FFA (mM) | 2-furancarboxylic acid (mM) |
|---|---|---|---|
| galacturonate (low) | 0.77 | 0.106 | 0 |
| galacturonate (high) | 2.83 | 0.430 | 0 |
| alginate (low) | 1.53 | 0.111 | 0 |
| alginate (high) | 2.62 | 0.295 | 0 |

Each starting material was combined with 98% sulfuric acid (2 mL) and sodium tetraborate decahydrate (75 mM). Each reaction mixture was heated to 70° C. After 10 minutes, a sample from each reaction mixture was obtained and analyzed by HPLC according to the procedure described in Example 8 above to determine the production of FFA.

Analysis

Table 8 above summarizes the product yields for FFA and 2-furancarboxylic acid observed in each reaction mixture. The data from this table was used to generate FIGS. 17 and 18.

Figure 17:
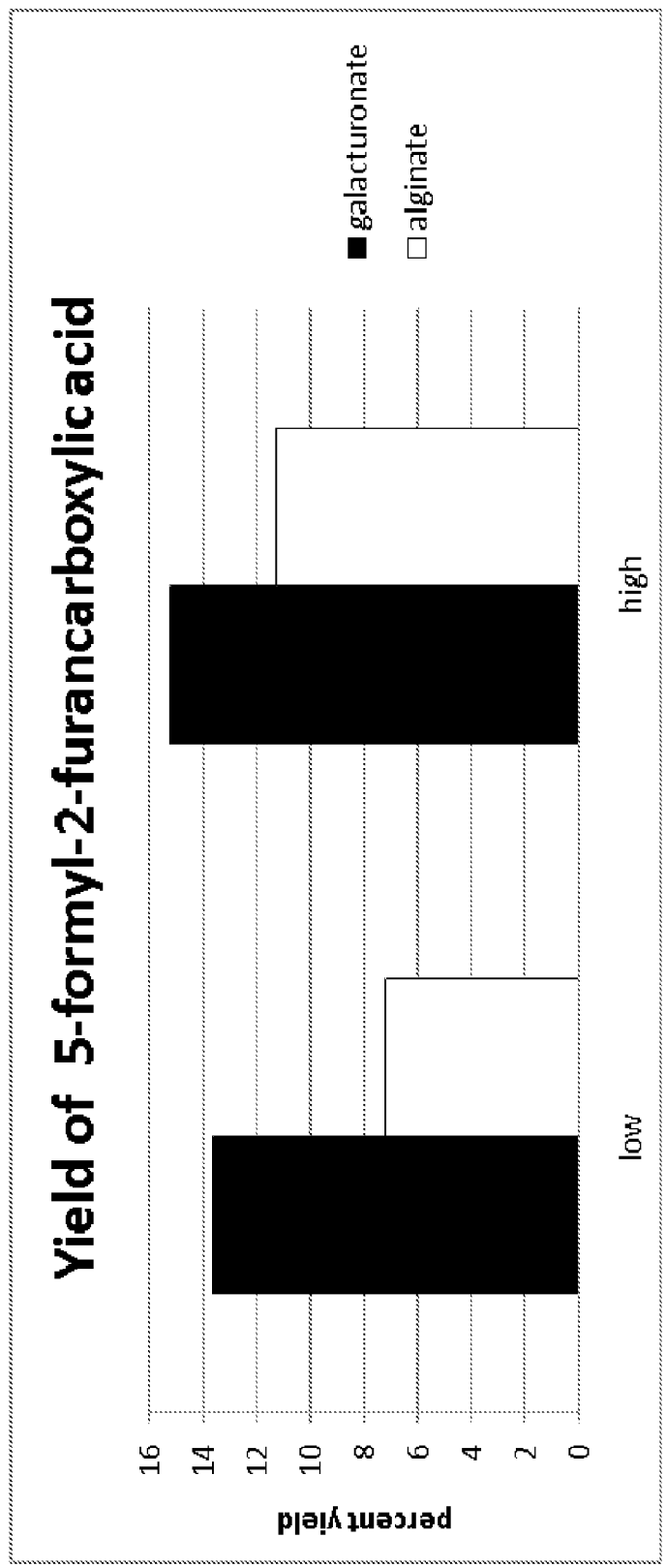
FIG. 17 is a graph depicting the yield of FFA produced from (a) galacturonate and (b) alginate in the presence of sulfuric acid and sodium tetraborate decahydrate.

As seen FIG. 17, FFA was observed in all the reactions. There was no significant difference between the yield of FFA produced in the higher versus low concentration reactions, although it was observed that the higher concentration reaction had a higher yield than the lower concentration reaction for both galacturonate and alginate.

Figure 18:
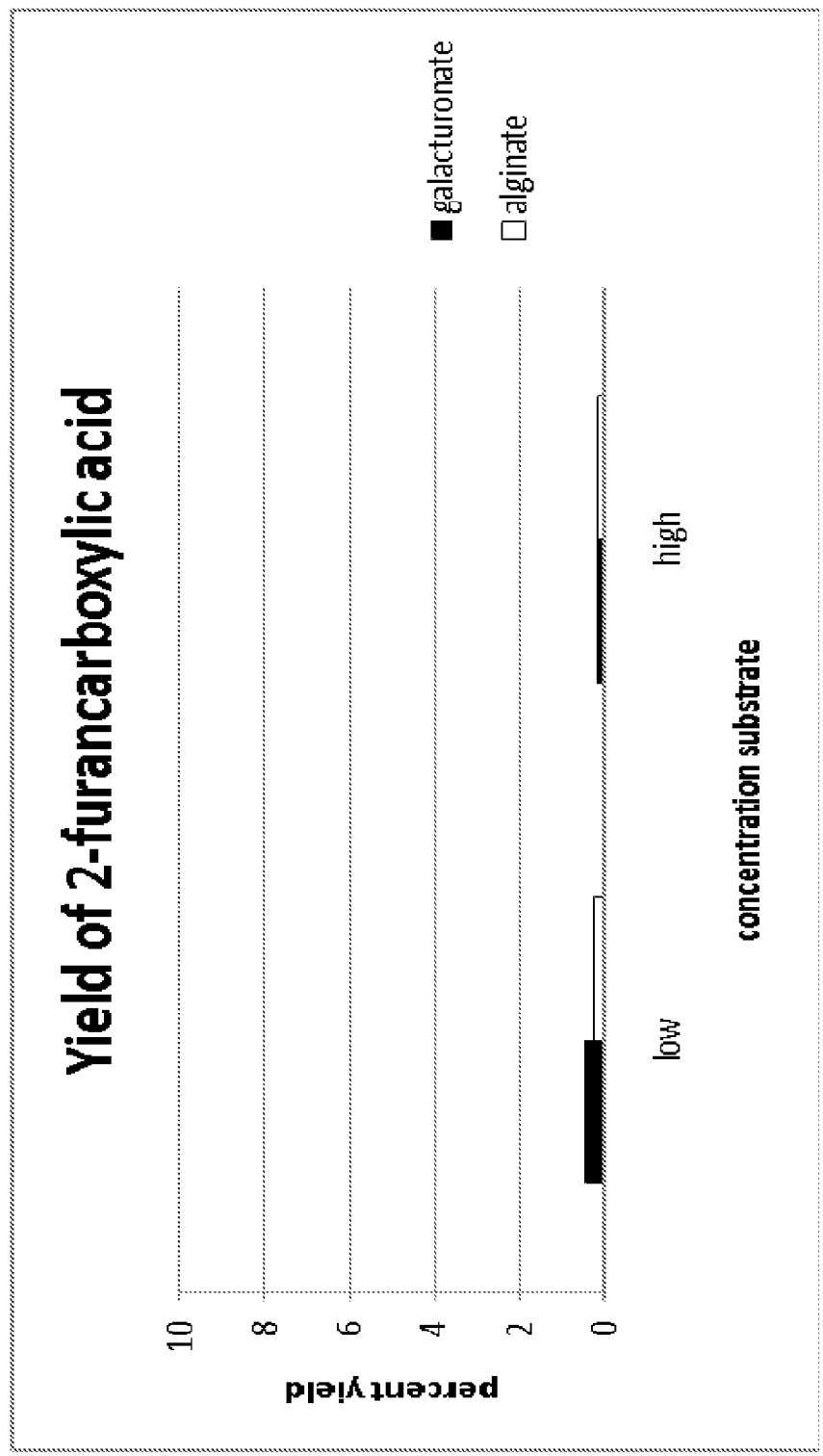
FIG. 18 is a graph depicting the yield of 2-furancarboxylic acid produced from (a) galacturonate and (b) alginate in the presence of sulfuric acid and sodium tetraborate decahydrate.

As seen in FIG. 18, trace amounts of 2-furancarboxylic acid were observed in the reaction mixtures.

Example 10

Conversion of Galacturonate, Alginate and Oligoalginate into FFA

This example demonstrates the acid-catalyzed dehydration and cyclization of galacturonate, alginate and oligoalginate (produced by enzymatically degrading alginate with sigma alginate lyase) to yield FFA in the presence of five different sulfuric acid treatments and sodium tetraborate decahydrate.

Materials and Methods

The starting materials in this example include galacturonate, alginate, and degraded alginate (i.e., oligoalginate). The concentrations of starting materials used in each of the reactions described in this example are summarized in Table 9 below.

analyzed by HPLC according to the procedure described in Example 8 above to determine the production of FFA.

Analysis

Table 9 above summarizes the product yields for FFA and 2-furancarboxylic acid observed in each reaction mixture. The data from this table was used to generate FIGS. 19 and 20.

Figure 19:
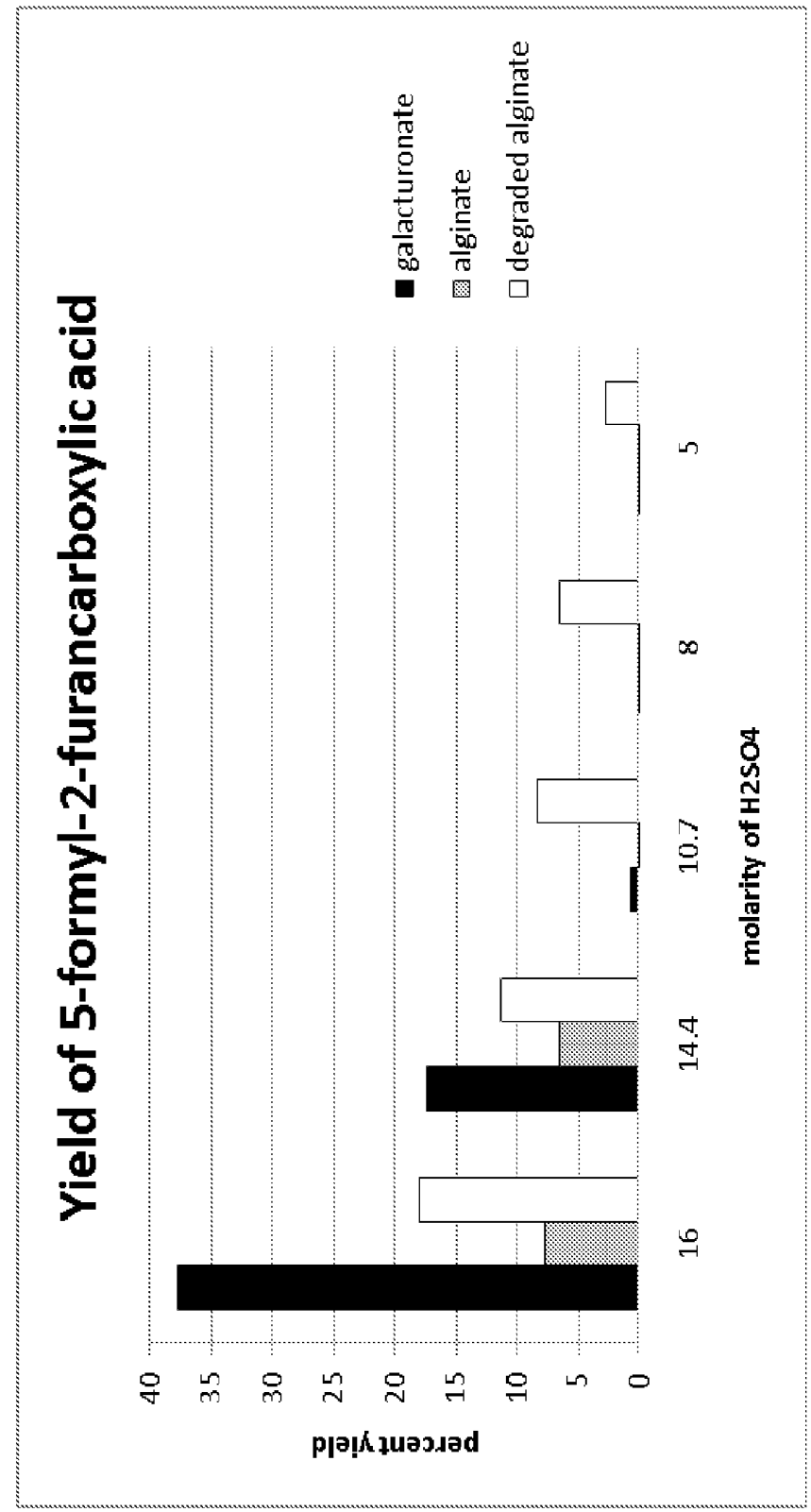
FIG. 19 is a graph depicting the yield of FFA produced from (a) galacturonate, (b) alginate, and (c) degraded alginate (i.e., oligoalginate) using sulfuric acid treatments of 16 M, 14.4 M, 10.7 M, 8M, and 5M concentrations.

As seen in FIG. 19, degraded alginate (oligoalginate) was observed to produce FFA in all reactions, whereas galacturonate and alginate were observed to produce FFA at 16 M and 14.4 M sulfuric acid treatments. The stronger acid treatments were observed to produce higher FFA yields.

Figure 20:
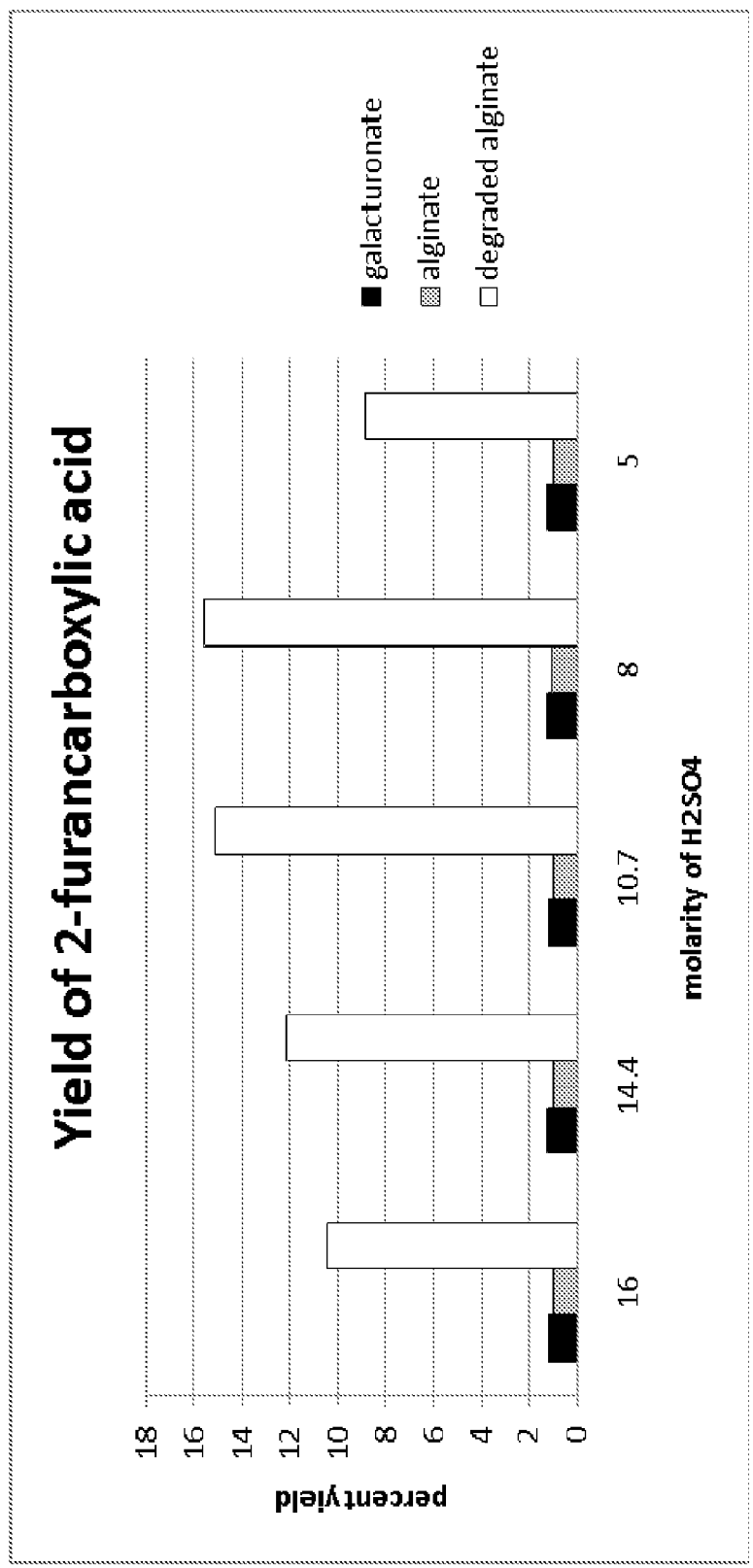
FIG. 20 is a graph depicting the yield of 2-furancarboxylic acid produced from (a) galacturonate, (b) alginate, and (c) degraded alginate (i.e., oligoalginate) using sulfuric acid treatments of 16 M, 14.4 M, 10.7 M, 8M, and 5M concentrations.

As seen in FIG. 20, degraded alginate (oligoalginate) was observed to produce more 2-furancarboxylic acid in the reaction mixture than galacturonate and alginate. It was also observed that for the degraded alginate reactions, the 10.7 M

TABLE 9

Summary of the concentration starting materials, and products (FFA and 2-furancarboxylic acid)

| Acid treatment | Starting material | Starting material concentration (mM) | FFA (mM) | 2-furancarboxylic acid (mM) |
|---|---|---|---|---|
| 16M $H_2SO_4$ | galacturonate | 0.32 | 0.119 | 0 |
| 16M $H_2SO_4$ | alginate | 0.38 | 0.029 | 0 |
| 16M $H_2SO_4$ | degraded alginate | 0.37 | 0.066 | 0.039 |
| 14.4M $H_2SO_4$ | galacturonate | 0.31 | 0.054 | 0 |
| 14.4M $H_2SO_4$ | alginate | 0.38 | 0.024 | 0 |
| 14.4M $H_2SO_4$ | degraded alginate | 0.37 | 0.041 | 0.044 |
| 10.7M $H_2SO_4$ | galacturonate | 0.32 | 0.002 | 0 |
| 10.7M $H_2SO_4$ | alginate | 0.38 | 0 | 0 |
| 10.7M $H_2SO_4$ | degraded alginate | 0.37 | 0.031 | 0.056 |
| 8M $H_2SO_4$ | galacturonate | 0.30 | 0 | 0 |
| 8M $H_2SO_4$ | alginate | 0.37 | 0.000 | 0 |
| 8M $H_2SO_4$ | degraded alginate | 0.36 | 0.023 | 0.055 |
| 5M $H_2SO_4$ | galacturonate | 0.31 | 0 | 0 |
| 5M $H_2SO_4$ | alginate | 0.38 | 0 | 0 |
| 5M $H_2SO_4$ | degraded alginate | 0.37 | 0.010 | 0.032 |

In the first acid treatment, each of starting materials was combined with water (0.125 mL), 98% sulfuric acid (2 mL), and sodium tetraborate decahydrate (75 mM). The final sulfuric acid concentration was 16 M.

In the second acid treatment, each starting material was combined with water (0.375 mL), 98% sulfuric acid (2 mL), and sodium tetraborate decahydrate (75 mM). The final sulfuric acid concentration was 14.4 M.

In the third acid treatment, each starting material was combined with water (0.125 mL), 72% sulfuric acid (2 mL), and sodium tetraborate decahydrate (75 mM). The final sulfuric acid concentration was 10.7 M.

In the fourth acid treatment, each starting material was combined with water (0.875 mL), 72% sulfuric acid (2 mL), and sodium tetraborate decahydrate (75 mM). The final sulfuric acid concentration was 8 M.

In one reaction of the fifth acid treatment, each starting material was combined with water (1.275 mL), 72% sulfuric acid (1 mL), and sodium tetraborate decahydrate (75 mM). The final sulfuric acid concentration was 5 M.

Each reaction mixture was heated to 70° C. After 10 minutes, a sample from each reaction mixture was obtained and and 8 M sulfuric acid treatments yielded a higher percentage of 2-furancarboxylic acid compared to the other acid treatments.

Example 11

Conversion of Alginate, Oligoalginate, and DEHU into FFA Using HCl

This example demonstrates the acid-catalyzed dehydration and cyclization of alginate, oligoalginate, and DEHU into FFA based on reaction of the substrates with 12 wt/v % hydrochloric acid.

Materials and Methods

The starting materials in this example include alginate, oligoalginate and DEHU. The concentrations of starting materials used in each of the reactions described in this example are summarized in Table 10 below.

TABLE 10

Summary of the concentration starting materials, and products (FFA, 2-furancarboxylic acid and furfural)

| Starting material | Starting material concentration (mM) | FFA (mM) | 2-furancarboxylic acid (mM) | Furfural (mM) |
|---|---|---|---|---|
| Alginate | 10.2 | 0 | 0 | 0.11 |
| Oligoalginate | 10.4 | 0.44 | 0.78 | 0.26 |
| DEHU | 10.1 | 0.15 | 0.70 | 0 |

Each reaction mixture was heated to 100° C. After 2 hours, a sample from each reaction mixture was obtained and analyzed by HPLC according to the procedure described in Example 1 above to determine the production of FFA.

Analysis

Table 10 above summarizes the product yields for FFA, FA and furfural observed in each reaction mixture. The data from this table was used to generate FIG. 21.

Figure 21:
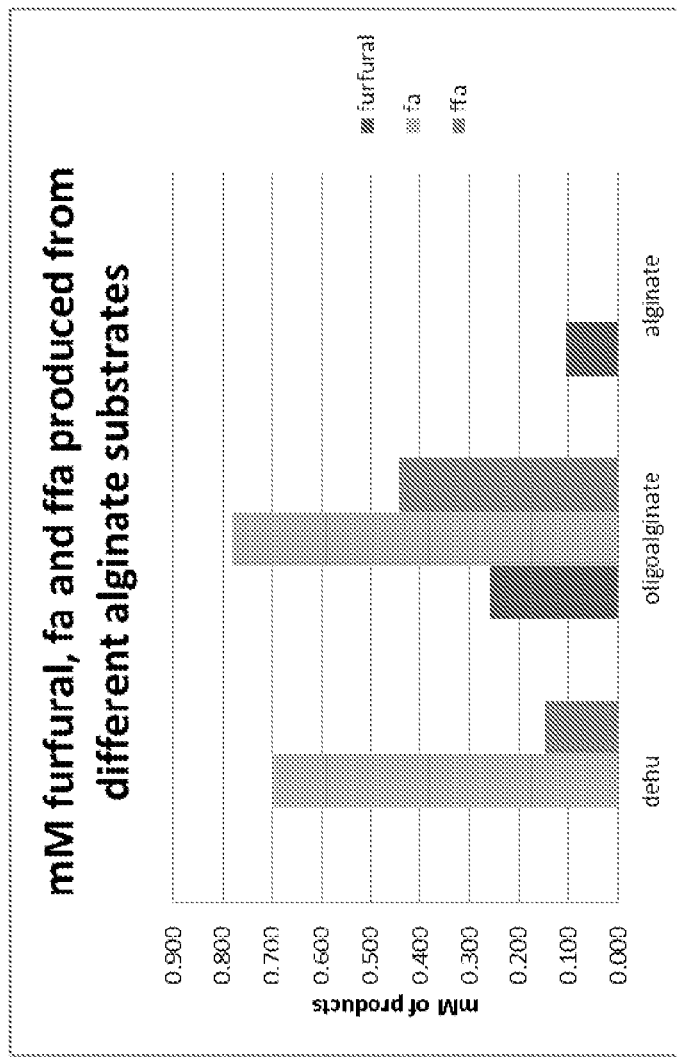
FIG. 21 is a graph depicting the production of FDCA and consumption of FFA over 24 hours.

As seen in FIG. 21, FFA was observed the most in oligoalginate showing that the median polymer degradation produced the most product.

Example 12

Figure 22:
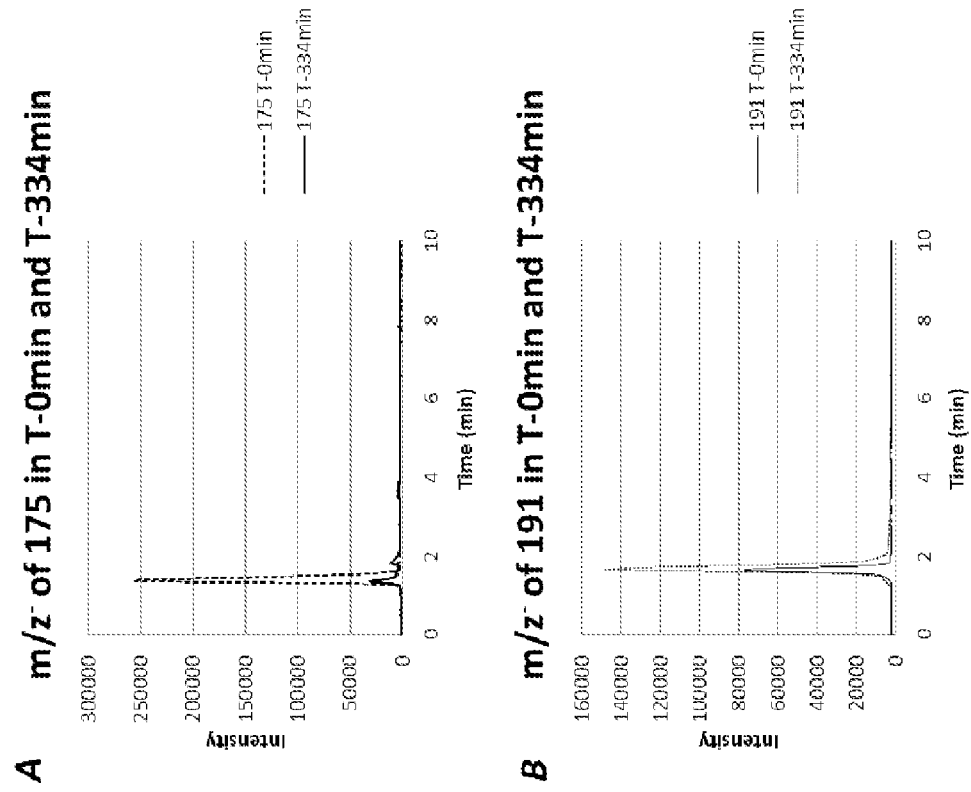
FIG. 22 includes two graphs depicting the conversion of DEHU (m/z⁻=175.

Conversion of DEHU into DOHA 0.1740 grams of 5% platinum on carbon catalyst was added to water with low dissolved oxygen. The dissolved oxygen was depleted by blowing nitrogen gas through the water over the course of a few minutes. The catalyst was added to 600 ml of 1% degraded alginate solution in a 1 L reactor. To the dehu 5 ml of 1M pH 8.0 phosphate buffer was added. The pH was controlled to pH 9 using base. The temperature was at 50 C. The sample sat in the reactor for 2 days before being filtered. FIG. 22 depicts the conversion of DEHU to DOHA. FIG. 22A suggests DEHU (m/z$^-$=175) consumption at time 334 min after oxidation reaction started. FIG. 22B depicts the DOHA (m/z$^-$=191) production at time 334 min after oxidation reaction started.

Example 13

Conversion of DEHU into FDCA and FDCA Ethylesters

Oxidation

Forty five (45) mL of 3 wt % stock DEHU solution into which was dissolved 0.37 g anhydrous sodium acetate (Spectrum Chemicals, Cat #S1110) was placed in a 75 ml Parr stirred autoclave reactor (Parr 5000 Multireactor system, Parr Inc. Moline, Ill.) along with 1.0 g of 5 wt % platinum on carbon catalyst (Degussa type F101 RA/W, 50 wt % $H_2O$). The contents were stirred at 500 rpm during reaction. The reactor vessel was pressurized to 50 psig $O_2$ and heated to 50° C. The reaction was allowed to proceed for 19 hr. At the end of reaction, the vessel was cooled and depressurized. The contents were removed.

An amount of aqueous HCl (0.1 M, 45 ml) equal to the molar quantity of sodium acetate present in the reaction contents was added to lower pH.

Filtration and Drying

The reaction contents were vacuum filtered through a Buchner funnel to remove solid catalyst, dried in a rotary evaporator for 2 hr until forming a thick syrup, and then dried further under high vacuum (200 millitorr) for 2 hr. The amount of dried material recovered was 0.85 g.

Esterification and Dehydration

The dried reactor contents were dissolved in 20 ml ethanol solution containing 10 wt % $H_2SO_4$. The alcoholic solution was placed into a 75 ml Parr stirred autoclave reactor and heated to 100° C. for 15 hr. Following reaction, a significant amount of solid was observed on the bottom of the reactor vessel. The reaction solution was observed to have a transparent brown color ("Sample R19").

Analysis

The reactor contents were analyzed by HPLC according to the two methods described below, and were compared to several standards. First, a standard of FDCA ethyl esters, prepared by dissolving 0.1 g FDCA and with 0.1 g para-toluenesulfonic acid into 5 g ethanol and heating for 24 hr at 70° C., was used to identify the presence of both FDCA and FDCA esters in both liquid chromatographic methods. Both the free FDCA acid and the esters are present because the reaction does not proceed to completion. Second, a standard of FDCA was prepared by adding 10 mg FDCA to 2.0 ml water and heating to dissolve. Third, a mixed standard of FDCA and FFCA was prepared by adding 10 mg of each compound to 2.0 ml water and heating to dissolve.

HPLC Method 1: (Short)

Column: Supelco Discovery HS-F5 33×4.6 mm 3 um

Mobile phase: A 0.2% TFA in water

B 0.2% TFA in methanol

Gradient: 0-3 min: 80% A/20% B 3-7 min: 0% A/100% B 7-7.4 min: 80% A/20% B

Flow rate: 1.0 ml/min

Column temperature: 25° C.

Detection: UV 205 nm, 254 nm and ELSD

System: Shimazu LC-2010Aht system; Alltech 3300 ELSD

HPLC Method 2: (Long)

Column: Biorad Aminex HPX-87-H 300×7.8 mm

Mobile phase: 15 mM H2SO4

Flow: 0.55 ml/min

Column temperature: 40° C.

Injection: 5 μL

Detection: UV 205 nm and RI

System: Biorad 1350 hplc pump; Water 717+ injector; Hitachi L-4000H UV detector; Waters 410 Differential refractive index detector; Varian Star chromatograph data collection system

RESULTS

Figure 23A:
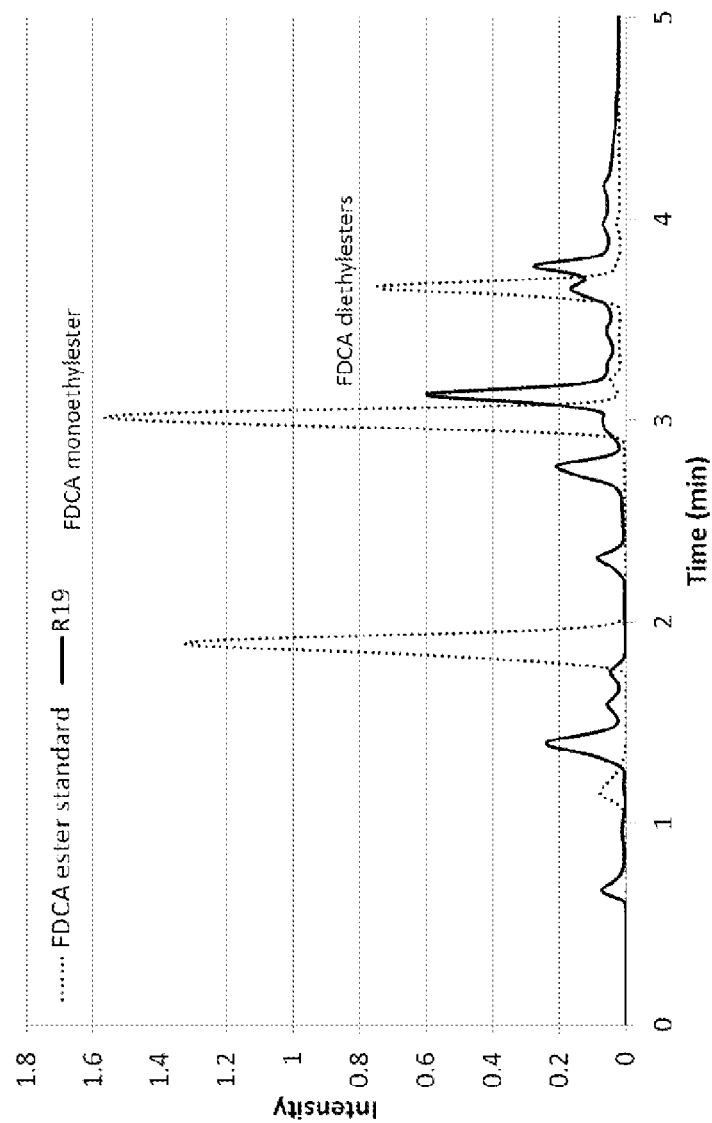
FIGS. 23A and 23B include two HPLC spectra, depicting the formation of FDCA, FDCA ethylester, and FDCA diethylester from DOHA.

With reference to FIG. 23A, an HPLC Chromatogram was obtained using a UV detector at 254 nm according to HPLC Method 1 described above. This HPLC indicated a peak at 1.9 minutes, corresponding to FDCA. Peaks at 3.0 minutes and 3.7 minutes were also observed, and corresponded to FDCA monoethylester and FDCA diethylester. An HPLC of Sample R19 revealed peaks corresponding to both FDCA esters.

Figure 23B:
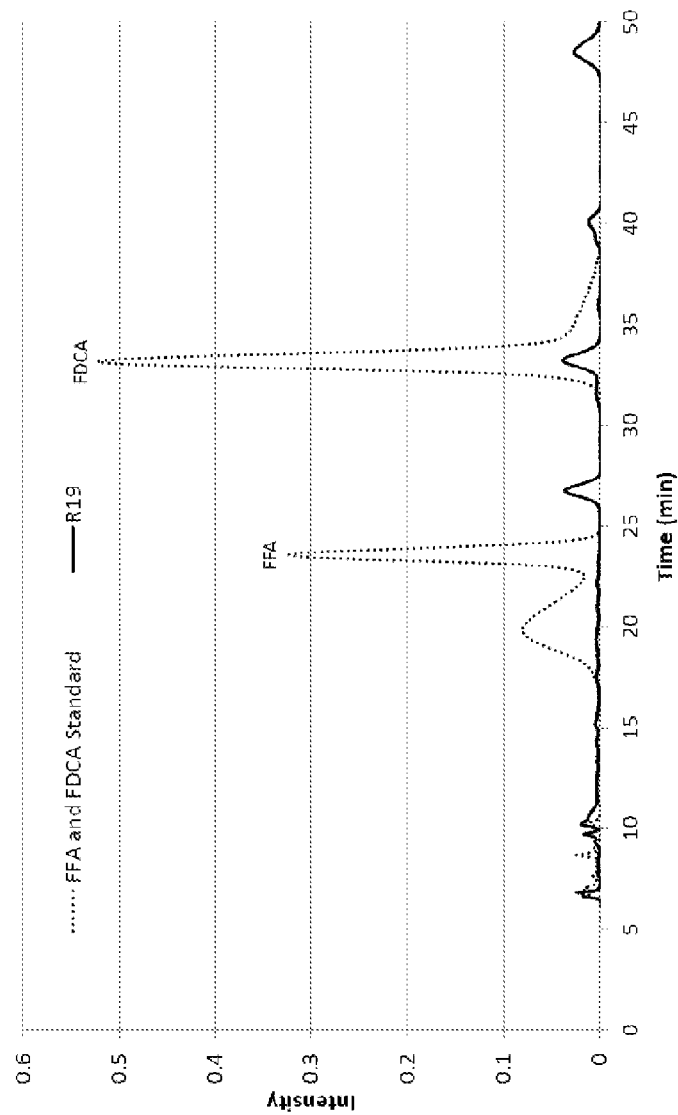

With reference to FIG. 23B, an HPLC chromatogram was obtained using a UV detector at 254 nm according to HPLC Method 2 described above. Peaks at 24 and 33.5 minutes represent FFA and FDCA, respectively. Additional a small peak corresponding to FDCA was seen in the HPLC analysis of Sample R19.

Figure 24:
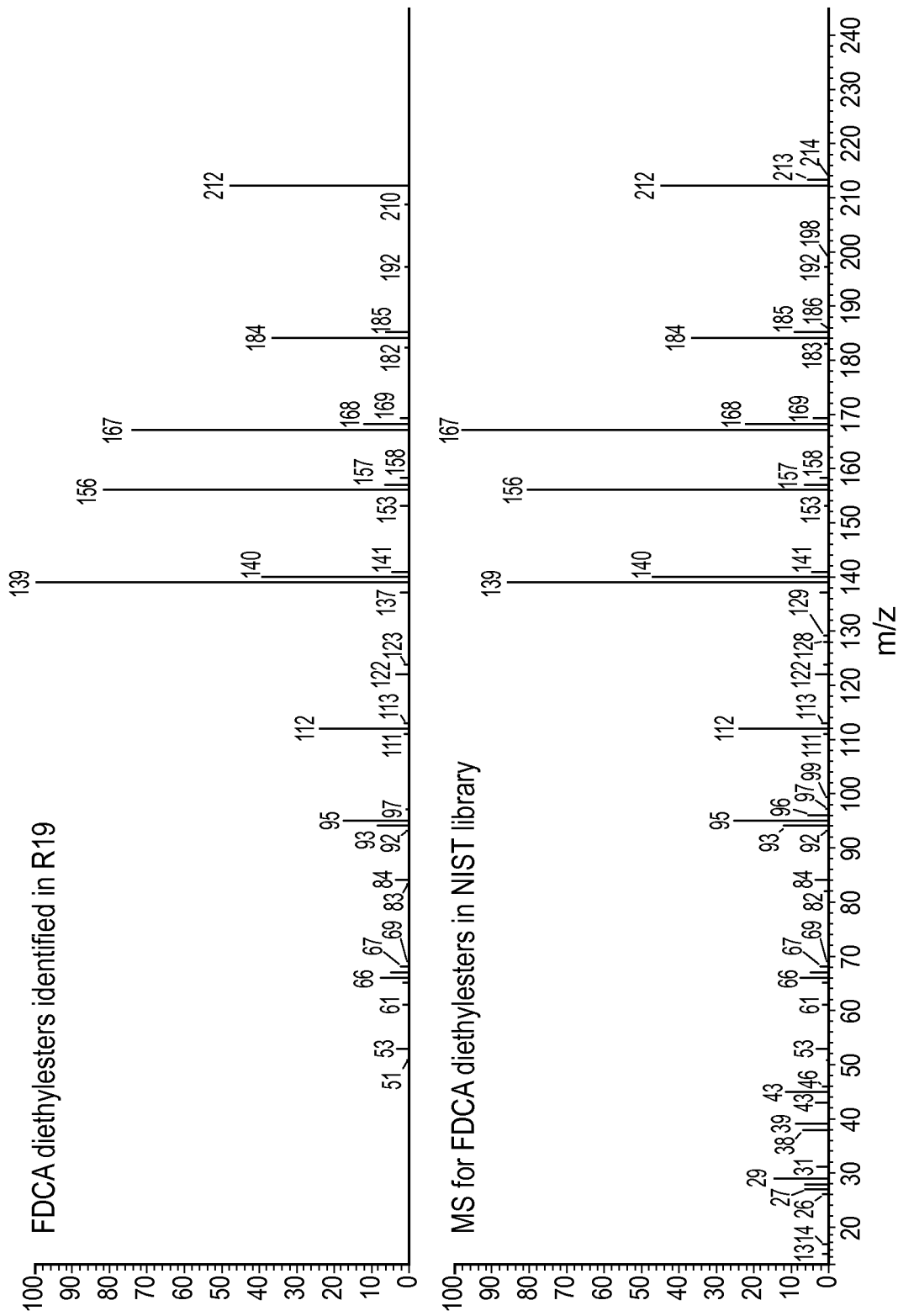
FIG. 24 includes two GC-MS spectra, depicting a comparison between the FDCA diethylester produced according to the procedure in Example 13 below and FDCA diethylester from the NIST library.

Additionally, with reference to FIG. 24B, the formation of the FDCA diethylester was confirmed by GC-MS.

What is claimed is:

1. A method of producing 2,5-furandicarboxylic acid (FDCA), comprising:
   a) providing a compound of Formula (I),

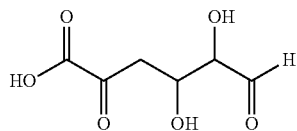

b) dehydrating and cyclizing the compound of formula I into 5-formyl-2-furancarboxylic acid (FFA); and
   c) oxidizing the FFA to produce FDCA.

2. The method of claim 1, wherein the compound of Formula (I) is 4-deoxy-L-erythro-5-hexoseulose uronate (DEHU), 4-deoxy-L-threo-5-hexosulose uronate (DTHU), or a mixture thereof.

3. A method of producing 2,5-furandicarboxylic acid (FDCA), comprising:
   a) providing 4-deoxy-L-erythro-5-hexoseulose uronate (DEHU);
   b) dehydrating and cyclizing the DEHU into 5-formyl-2-furancarboxylic acid (FFA); and
   c) oxidizing the FFA to produce FDCA.

4. The method of claim 3, wherein the dehydrating and cyclizing the DEHU comprises heating the DEHU at a temperature sufficient to form the FFA in the presence of a dehydration catalyst and optionally in the presence of a solvent.

5. The method of claim 3, wherein the dehydrating and cyclizing of the DEHU into FFA comprises combining the DEHU with a catalyst to form a reaction mixture.

6. The method of claim 5, wherein the catalyst is selected from the group consisting of oxalic acid, levulinic acid, maleic acid, p-toluenesulfonic acid, tetrafluoroethylene-perfluoro-3,6-dioxa-4-methyl-7-octenesulfonic acid copolymer, a silica nanocompositie solid acid catalyst, chloro acetic acid, fluoro acetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon, and a combination thereof.

7. The method of claim 5, wherein the dehydrating and cyclizing of the DEHU into FFA is performed neat.

8. The method of claim 5, wherein the dehydrating and cyclizing of the DEHU into FFA further comprises combining the reaction mixture with a solvent.

9. The method of claim 8, wherein the solvent is selected from the group consisting of water, methanol, ethanol, propanol, isopropanol, butanol, 2-butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, polyethylene glycol, methyl isobutyl ketone, and a combination thereof.

10. The method of claim 5, wherein the dehydrating and cyclizing of the DEHU into FFA further comprises heating the reaction mixture.

11. The method of claim 10, wherein the reaction mixture is heated to a temperature between 50° C. and 500° C.

12. The method of claim 3, wherein the oxidizing of FFA to produce FDCA comprises combining the FFA with an oxidant.

13. The method of claim 12, wherein the oxidant is bromine, nitric acid, peroxide, a platinum catalyst, a gold catalyst, a palladium catalyst, a rhodium catalyst, a copper catalyst, a molybdenum catalyst, a vanadium catalyst, a titanium catalyst, a cobalt catalyst, a nickel catalyst, an iron catalyst, and a combination thereof.

14. The method of claim 12, wherein the oxidant is platinum on a solid support.

15. The method of claim 12, wherein the oxidant is platinum on carbon, platinum on silica, platinum on titanium dioxide, or platinum on alumina.

16. The method of claim 12, wherein the oxidizing of FFA to produce FDCA further comprises combining the FFA and the oxidant with water.

17. The method of claim 3, wherein the method yields at least 20% of the theoretical maximum of FDCA that may be produced from DEHU.

18. A method of producing a compound of Formula (II), comprising:
   a) providing 4-deoxy-L-erythro-5-hexoseulose uronate (DEHU);
   b) oxidizing the DEHU to produce 2,3-dihydroxy-5-oxohexanedioic acid (DOHA); and
   c) dehydrating and cyclizing the DOHA into a compound of Formula (II)

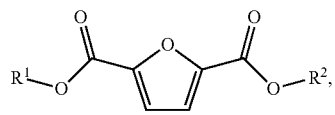

wherein (i) $R^1$ and $R^2$ are each independently H or $C_1$-$C_{20}$ alkyl, and (ii) when at least one of $R^1$ and $R^2$ is $C_1$-$C_{20}$ alkyl, then dehydrating and cyclizing is performed in the presence of an alkyl alcohol solvent having an alkyl substituent corresponding to the $C_1$-$C_{20}$ alkyl group and under conditions to form an ester of at least one of $R^1$ and $R^2$.

19. The method of claim 18, wherein $R^1$ and $R^2$ are both H.

20. The method of claim 18, wherein $R^1$ is H, and $R^2$ is $C_1$-$C_{20}$ alkyl.

21. The method of claim 18, wherein $R^1$ and $R^2$ are both $C_1$-$C_{20}$ alkyl.

22. The method of claim 18, wherein the oxidizing of DEHU to produce DOHA comprises combining DEHU with an oxidant.

23. The method of claim 18, wherein the dehydrating and cyclizing the DOHA comprises heating the DOHA at a temperature sufficient to form the compound of Formula (II) in the presence of a dehydration catalyst and optionally in the presence of a solvent.

24. The method of claim 18, wherein the dehydrating and cyclizing of the DOHA into the compound of Formula (II) comprises combining DOHA with a catalyst to form a reaction mixture.

25. A method of producing 2,5-furandicarboxylic acid (FDCA), comprising:
   a) providing 4-deoxy-L-threo-5-hexosulose uronate (DTHU);

b) dehydrating and cyclizing DTHU into 5-formyl 2-furancarboxylic 5-formyl-2-furancarboxylic acid (FFA); and
c) oxidizing the FFA to produce FDCA.

26. A method of producing 2,5-furandicarboxylic acid (FDCA), comprising:
   a) providing 4-deoxy-L-threo-5-hexosulose uronate (DTHU);
   b) oxidizing DTHU to produce 2,3-dihydroxy-5-oxohexanedioic acid (DOHA); and
   c) dehydrating and cyclizing the 2,3-dihydroxy-5-oxohexanedioic acid into FDCA.

27. A method of producing 5-formyl-2-furancarboxylic acid (FFA), comprising:
   a) providing 4-deoxy-L-erythro-5-hexoseulose uronate (DEHU) or 4-deoxy-L-threo-5-hexosulose uronate (DTHU); and
   b) dehydrating and cyclizing the DEHU or DTHU into 5-formyl-2-furancarboxylic acid (FFA).

28. The method of claim 27, further comprising isolating the FFA.

29. A method of producing 2,5-furandicarboxylic acid (FDCA), comprising:
   a) providing a starting material selected from the group consisting of alginate, oligoalginate, mannuronate, guluronate, pectin, oligopectin, polygalacturonate, oligogalacturonate, and a combination thereof;
   b) dehydrating and cyclizing the starting material into 5-formyl-2-furancarboxylic acid (FFA); and
   c) oxidizing the FFA to produce FDCA.

30. The method of claim 29, wherein the starting material is alginate or oligoalginate.

31. The method of claim 29, further comprising isolating the FDCA.

32. A method of producing 5-formyl-2-furancarboxylic acid (FFA), comprising:
   a) providing a starting material selected from the group consisting of alginate, oligoalginate, mannuronate, guluronate, pectin, oligopectin, polygalacturonate, oligogalacturonate, and a combination thereof;
   b) dehydrating and cyclizing the starting material into 5-formyl-2-furancarboxylic acid (FFA); and
   c) isolating the FFA.

33. The method of claim 29, wherein the starting material is selected from the group consisting of oligoalginate, mannuronate, guluronate, oligopectin, polygalacturonate, oligogalacturonate, and a combination thereof.

34. The method of claim 33, wherein the starting material is obtained by enzymatically degrading at least one of alginate and pectin.

35. The method of claim 32, wherein the starting material is selected from the group consisting of oligoalginate, mannuronate, guluronate, oligopectin, polygalacturonate, oligogalacturonate, and a combination thereof.

36. The method of claim 35, wherein the starting material is obtained by enzymatically degrading at least one of alginate and pectin.

* * * * *